(12) United States Patent
Meijer et al.

(10) Patent No.: US 8,450,342 B2
(45) Date of Patent: May 28, 2013

(54) PERHARIDINES AS CDK INHIBITORS

(75) Inventors: Laurent Meijer, Roscoff (FR); Karima Bettayeb, Roscoff (FR); Herve Galons, Paris (FR); Luc Demange, Paris (FR); Nassima Oumata, Paris (FR)

(73) Assignees: Centre Nationale de la Recherche Scientifique, Paris (FR); Universite de Rennes 1, Rennes (FR); Universite Paris Descartes, Paris (FR)

( * ) Notice: Subject to any disclaimer, the term of this patent is extended or adjusted under 35 U.S.C. 154(b) by 249 days.

(21) Appl. No.: 12/709,222

(22) Filed: Feb. 19, 2010

(65) Prior Publication Data

US 2010/0280065 A1 Nov. 4, 2010

Related U.S. Application Data

(63) Continuation-in-part of application No. PCT/IB2008/003106, filed on Sep. 12, 2008.

(51) Int. Cl.
*A61K 31/437* (2006.01)
*C07D 471/14* (2006.01)

(52) U.S. Cl.
USPC .......................................... 514/303; 546/118

(58) Field of Classification Search
USPC .......................................... 514/303; 546/118
See application file for complete search history.

(56) References Cited

U.S. PATENT DOCUMENTS 7,718,651 B2 * 5/2010 White et al. .................. 514/221

FOREIGN PATENT DOCUMENTS

| EP | 1 352 910 A1 | 10/2003 |
|---|---|---|
| WO | WO 2006/021803 A2 | 3/2006 |
| WO | WO 2006/027366 A1 | 3/2006 |

OTHER PUBLICATIONS

Bach et al.; "Roscovitine Targets, Protein Kinases and Pyridoxal Kinase;" *The Journal of Biological Chemistry*; Sep. 2, 2005; pp. 31,208-31,219; vol. 208, No. 35; JBC Papers in Press; U.S.A.
International Search Report mailed on Jun. 29, 2009 in corresponding International Application No. PCT/IB2008/003106.
Written Opinion of the International Searching Authority mailed on Jun. 29, 2009 in corresponding International Application No. PCT/IB2008/003106.
Bettayeb et al., *Small-molecule inducers of Aβ-42 peptide production share a common mechanism of action FASEB J* fj.12-212985; published ahead of print Sep. 12, 2012, doi:10.1096/ff.12-212985.

* cited by examiner

*Primary Examiner* — Samantha Shterengarts
(74) *Attorney, Agent, or Firm* — Oliff & Berridge, PLC

(57) ABSTRACT

The invention relates to trisubstituted or tetrasubstituted imidazo[4,5b]pyridines, to their uses as well as to a process for manufacturing them.
The compounds of the invention are imidazo[4,5b]pyridines. The first general synthesis of 3,5,7 imidazo[4,5b]pyridines is disclosed in the description.
The invention founds application, in particular, in the pharmaceutical field.

15 Claims, 16 Drawing Sheets

PERHARIDINES AS CDK INHIBITORS

Figure 1:
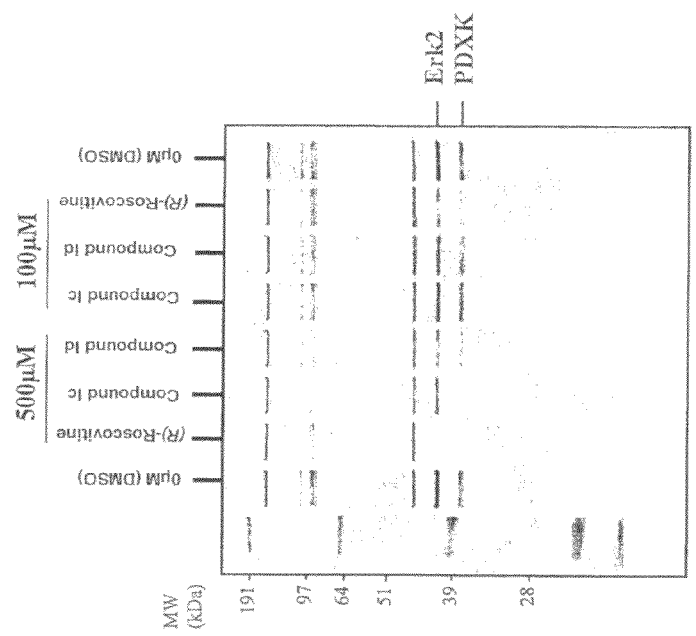

The invention relates to trisubstituted or tetrasubstituted imidazo[4,5-b]pyridines, to their uses as well as to a process for manufacturing them.

Cyclin-dependent kinases (CDKs) play an important role of regulator in the regulation of cell division, apoptosis, transcription, neuronal functions, and exocytosis.

The frequent deregulation of CDKs in human tumors and the involvement of CDK5 in Alzheimer's, Parkinson's and Nieman-Pick diseases, isehemia and stroke, as well as in various kidney diseases such as mesangial proliferative glomerulonephritis, crescentic glomerulonephritis, collapsing glomerulopathy, proliferative lupus nephritis, polycystic kidney diseases (PKD), diabetic nephropathy and acute kidney injury, cisplatin-induced nephrotoxicity, in inflammation such as in pleural inflammation, arthritis, glaucoma, in type 2 diabetes, in viral infections (HSV, HCMV, HPV, HIV), in unicellular parasite diseases such as those due to Plasmodium, Leishmania, etc. . . . have stimulated an active search for chemical CDK inhibitors.

Among the numerous inhibitors that have been identified, Roscovitine, one of the early compounds, appears to be relatively potent and selective.

Roscovitine is a purine having the following formula:

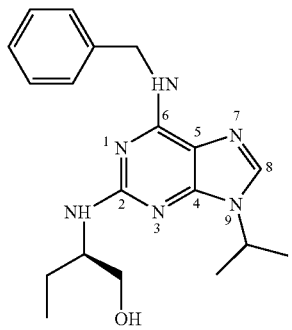 [SMILES: CC[C@H](CO)Nc1nc(NCc2ccccc2)c2ncn(C(C)C)c2n1]

Because of its cell growth inhibiting and neuroprotective activities, this purine is currently considered as a potential drug to treat, respectively, cancers, renal diseases, various neurodegenerative diseases and inflammations.

Besides, the selectivity of pharmacological inhibitors of protein kinases is an important issue and Roscovitine is a relatively selective CDKs inhibitor compared to other inhibitors, including the already commercialised inhibitor Gleevec®.

However, Roscovitine interacts with pyridoxal kinase.

A study of the interaction of Roscovitine and its derivatives with pyridoxal kinase is reported in Tang et al, J. Biol. Chem., 280, 35, Sep. 2, 2005, 31220-31229.

Pyridoxal kinase catalyzes the phosphorylation of pyridoxal, pyridoxamine and pyridoxine in the presence of ATP and $Zn^{2+}$. This constitutes an essential step in the synthesis of pyridoxal 5'-phosphate, the active form of vitamin $B_6$, a cofactor for over 140 enzymes. Interaction with the pyridoxal kinase system is thus likely to lead to unwanted side effects.

Thus, such an interaction is, on the one hand, detrimental to the synthesis of the active form of vitamine $B_6$, and/or, on the other hand, detrimental to the availability of Roscovitine and its derivatives, in patients treated with this type of CDKs inhibitors.

Therefore, the aim of the invention is to provide derivatives of Roscovitine having CDKs inhibitor properties but less or no interaction with pyridoxal kinase.

For this aim, the invention proposes compounds of the following formula I:

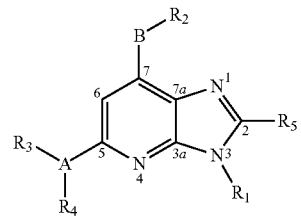

Formula I wherein:
A is CH or N or O,
$R_3$ is:
  H, or
  a $C_1$-$C_5$ alkyl group, or
  =O, or
  a ($C_1$-$C_3$) alkyl-C=O group in which the alkyl group is optionally substituted by one or more halogen atoms, and/or hydroxy groups, and/or amino groups, and/or alkyloxy groups, and/or ketone groups,
$R_4$ is:
  H, or
  a $C_1$-$C_6$ alkyl group optionally substituted by one or more halogen atoms, and/or hydroxy groups, and/or amino groups, and/or alkyloxy groups, and/or ketone groups,
  a $C_3$-$C_6$ cycloalkyl group optionally substituted by one or more halogen atoms, and/or hydroxy groups, and/or amino groups, and/or alkyloxy groups, and/or ketone groups, or
  a ($C_1$-$C_5$)alkyl($C_3$-$C_6$)cycloalkyl group optionally substituted by one or more halogen atoms, and/or hydroxy groups, and/or amino groups, and/or alkyloxy groups, and/or ketone groups, or
  =O, or
  O=$CCF_3$, or
  a $C_1$-$C_6$ alkyl group substituted by an ester group such as a O-acyl group, or an amino acyl group derived from natural, or non natural amino acids, or an acetyl group or a nicotinyl group,
or A, $R_3$ and $R_4$ together form a $C_5$-$C_7$ cycloalkyl group, optionally containing one or more heteroatoms, preferably a piperazine group,
B is O or S or NH or a halogen atom,
$R_1$ is:
  a $C_1$-$C_6$ alkyl group optionally branched and/or optionally substituted by one or more hydroxy groups, or
  a $C_3$-$C_6$ cycloalkyl group optionally substituted by one or more hydroxy groups, or
  an aryl group optionally substituted by one or more halogen atoms, and/or hydroxy groups, and/or $C_1$-$C_3$ alkyloxy groups, and/or optionally containing one or more heteroatoms, or
  a $C_1$-$C_5$ alkylaryl group, the aryl group being optionally substituted by one or more halogen atoms, and/or hydroxy groups, and/or $C_1$-$C_3$ alkyl groups, and/or $C_1$-$C_3$ alkyloxy groups, and/or optionally containing one or more heteroatoms, R₂ is:
- an aryl group optionally substituted by one or more halogen atoms, and/or hydroxy groups, and/or $C_1$-$C_3$ alkyloxy groups, and/or carboxylic acid groups, and/or carboxylic ester groups, and/or amine groups, and/or $CF_3$ groups, and/or optionally containing one or more heteroatoms, thus creating a 2-pyridyl group, or a 3-pyridyl group, or a 4-pyridyl group, or a 2-thienyl or a 3-thienyl group, or
- a methylbiaryl group, wherein each aryl cycle is optionally substituted by one or more halogen atoms, and/or hydroxy groups, and/or $C_1$-$C_3$ alkyloxy groups, and/or $CF_3$ groups, and/or carboxylic acid groups, and/or carboxylic ester groups, and/or amine groups, and/or optionally containing one or more heteroatoms, or
- a methylaryl group, the aryl cycle being optionally substituted by one or more halogen atoms, and/or hydroxy groups, and/or $C_1$-$C_3$ alkyloxy groups, and/or $CF_3$ groups, and/or optionally containing one or more heteroatoms, thus creating a 2-pyridyl group, or a 3-pyridyl group, or a 4-pyridyl group, or a 2-thienyl group or a 3-thienyl group,
- a biaryl group, each aryl cycle optionally containing one or more heteroatoms thus creating a 2-pyridyl group, or a 3-pyridyl group, or a 4-pyridyl group, or a 2-thienyl group or a 3-thienyl group, or each aryl cycle is optionally substituted by one or more halogen atoms, and/or hydroxy groups, and/or $C_1$-$C_3$ alkyloxy groups, and/or $CF_3$ groups, and/or carboxylic acid groups, and/or carboxylic ester groups, and/or amine groups, or B and R₂ together form a non aromatic cycle, R₅ is:
- a halogen atom, or
- a hydrogen atom, or
- a $C_1$-$C_5$ alkyl group optionally substituted by one or more hydroxy groups and/or amine groups and/or halogen atoms and/or carboxylic acid groups, or
- a ($C_1$-$C_4$)alkyl($C_3$-$C_6$)cycloalkyl group in which the cycloalkyl group is optionally substituted by one or more hydroxy groups and/or amine groups and/or halogen atoms and/or carboxylic acid groups, and the salts, hydrates, and stereoisomers thereof.

As used herein, the term "biaryl" designates two aryl cycles linked by a single bond and the term "carboxylic acid group" designates a —COOH group.

In a first preferred embodiment of the invention, in Formula I, A is N.

In a second preferred embodiment of the invention, in Formula I, A is CH.

In a third preferred embodiment of the invention, in Formula I, A is O.

In each of the preferred embodiment of the invention, in Formula I, preferably R1 group is an ethyl, or a methyl, or an isopropyl, or a methylcyclopropyl, or a cyclopentyl, a phenyl group, or a benzyl group or a methylpyridyl group, or

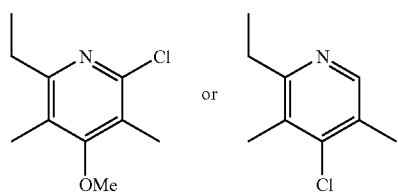

or

In each of the preferred embodiments of the invention, in Formula I, preferred B—R₂ group is one of those identified in the following table 1:

TABLE 1

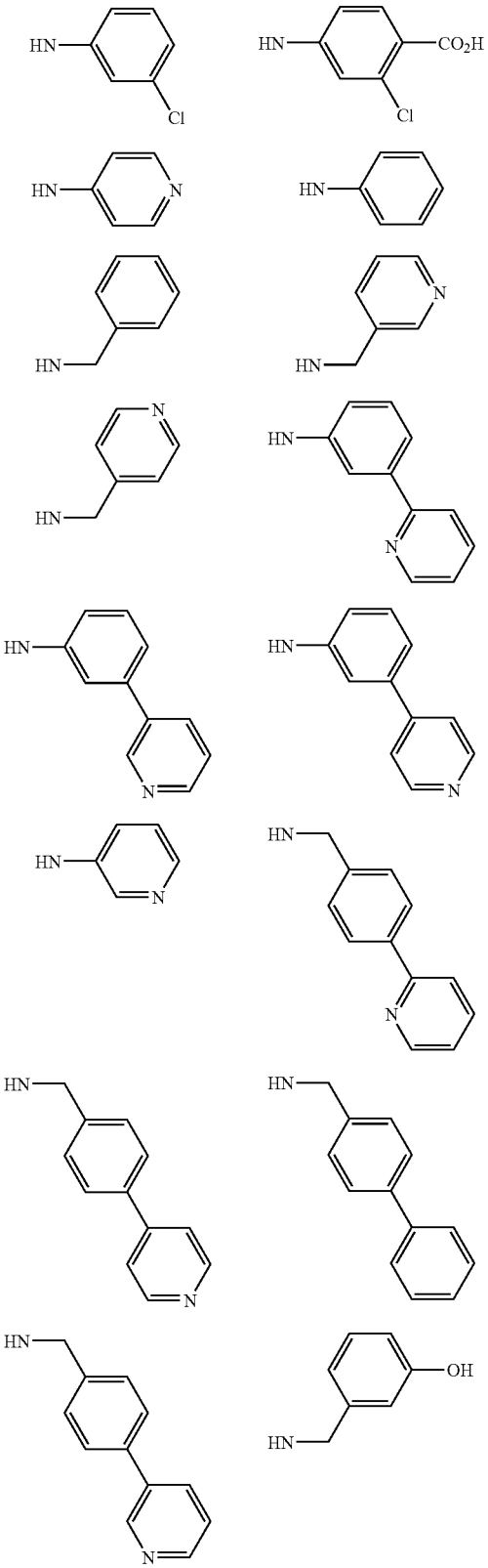

TABLE 1-continued

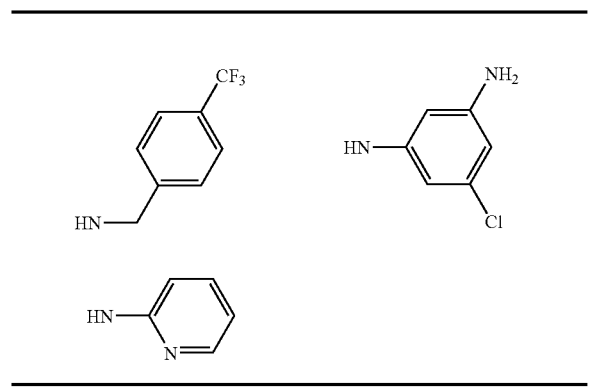

Still in each of the preferred embodiments of the invention, in Formula I, preferably the $R_4$-A-$R_3$ substituent is one of the groups identified in the following table 2:

TABLE 2

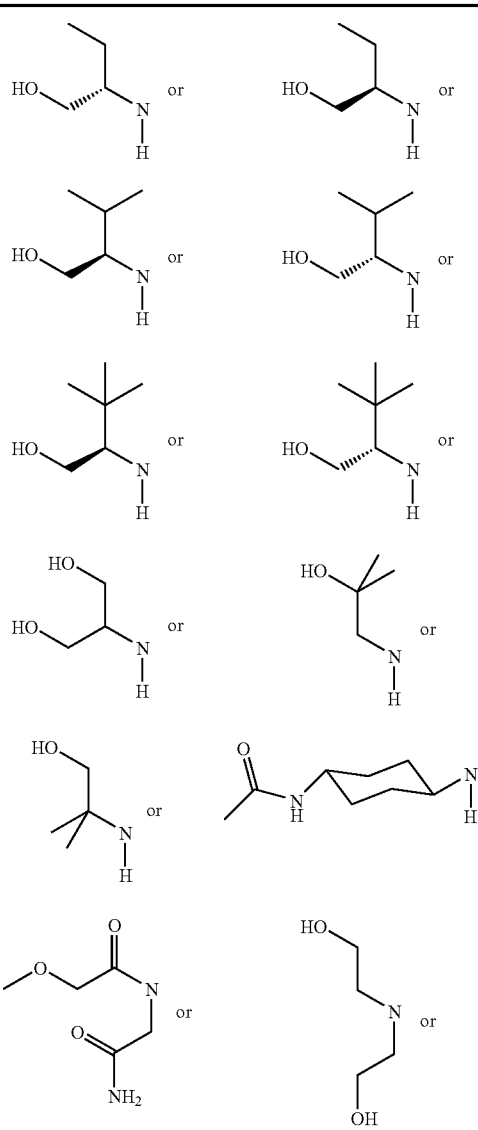

TABLE 2-continued

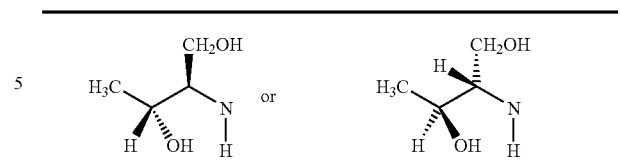

Other R4-A-R3 groups may be chosen among:

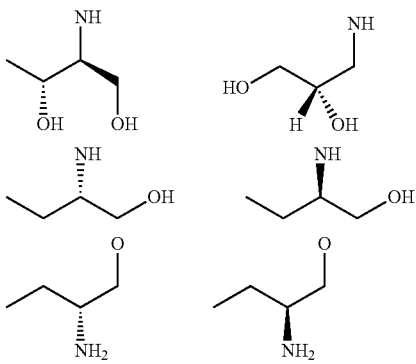

Furthermore, in each of the preferred embodiments of the invention, preferably $R_4$-A-$R_3$ is an ester functionality.

Indeed, although these esters exhibit moderate or low in vitro activity, they behave in vivo as prodrugs of the bioactive compounds of Formula I of the invention.

In such prodrugs, which are esters of the compound of formula I of the invention, preferred $R_4$-A-$R_3$ groups are those identified in the following table 3.

TABLE 3

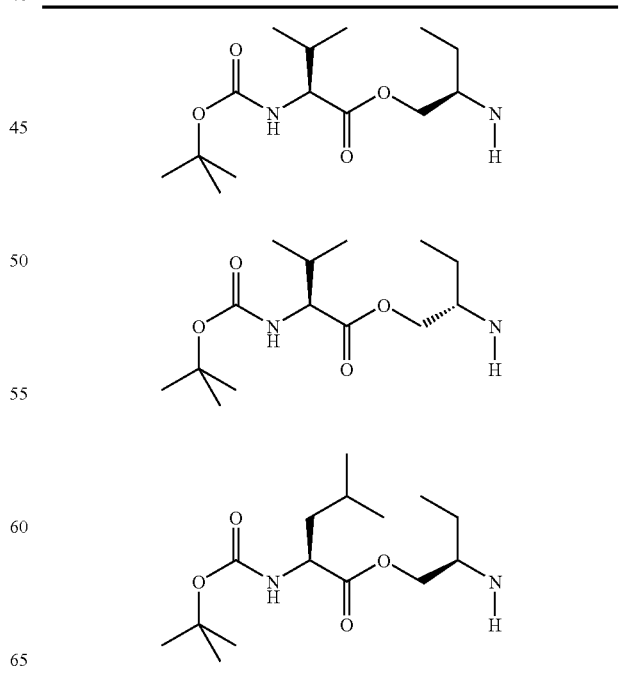

TABLE 3-continued

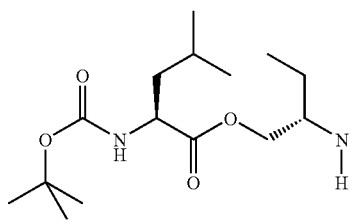 [SMILES: CC[C@H](N)COC(=O)[C@H](CC(C)C)NC(=O)OC(C)(C)C]
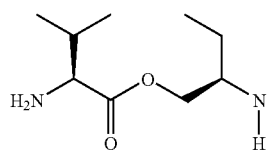
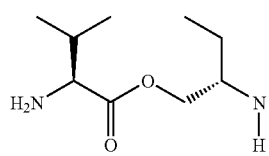
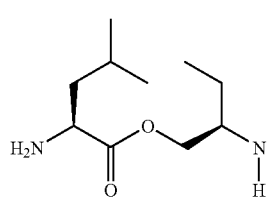
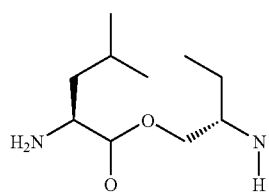
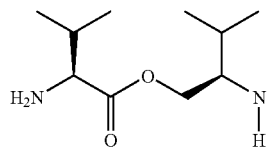
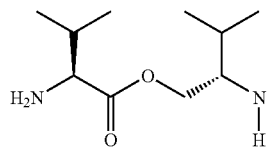
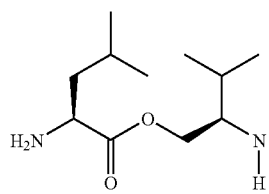

TABLE 3-continued

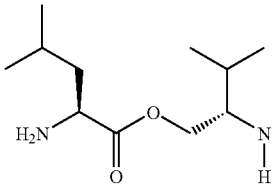

A preferred compound of the invention is the compound having the following formula Ia:

Formula Ia

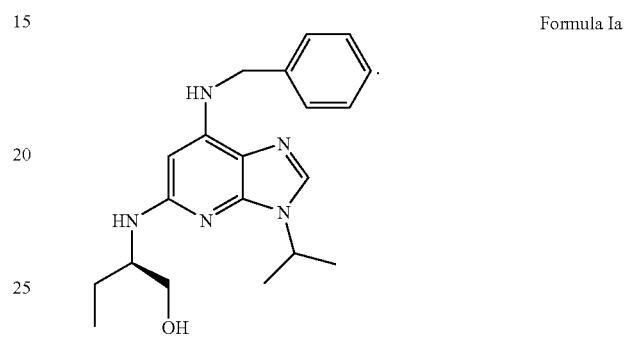

This compound has an absolute configuration (R) and is hereinafter also referred to as "perharidine A".

But, the (S) isomer of perharidine A, having the following formula Ib, is also preferred:

Formula Ib

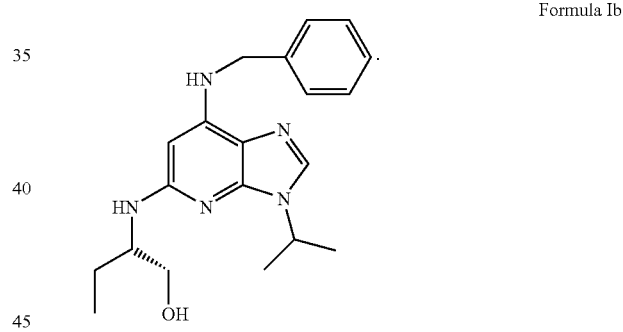

This compound is hereinafter also referred to as "perharidine B".

Another preferred compound of the invention has the following formula Ic:

Formula Ic

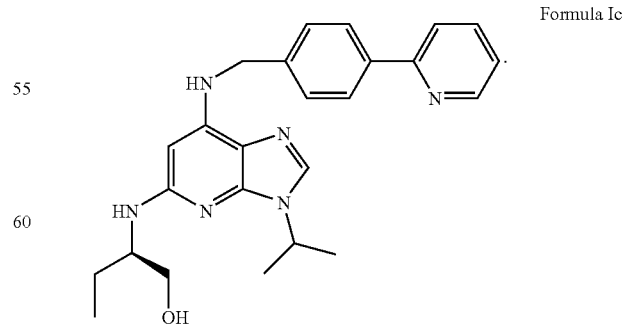

This compound is hereinafter also referred to as "perharidine C".

Still another preferred compound of the invention has the following formula Id:

Formula Id

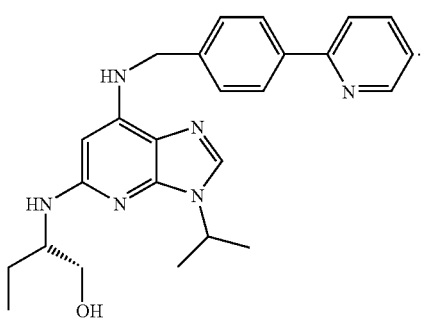

This compound is hereinafter also referred to as "perharidine D".

But the compound of the invention having the following formula Ie is also preferred:

Formula Ie

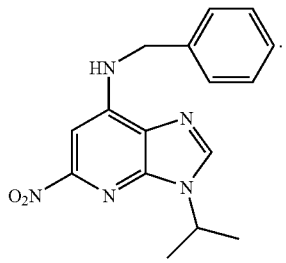

The compound of the invention having the following formula If is also a preferred compound:

Formula If

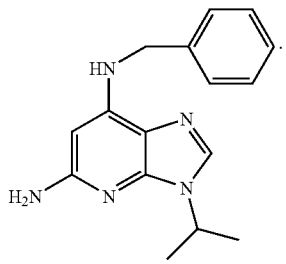

The compound of the invention having the following formula Ig is also preferred:

Formula Ig

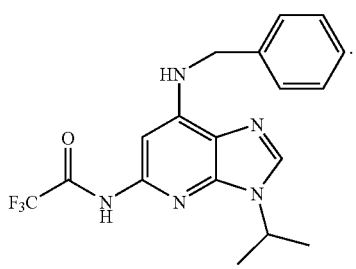

Furthermore, the compound of the invention having the following formula Ih is also preferred.

Formula Ih

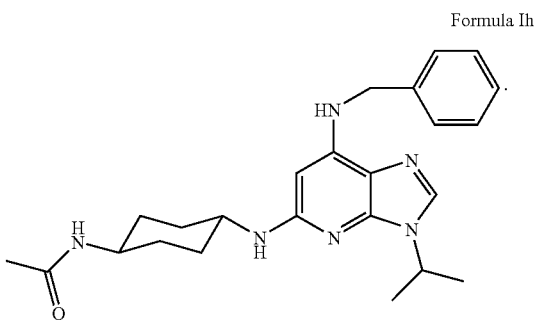 [SMILES: CC(=O)NC1CCC(Nc2cc(NCc3ccccc3)c3ncn(C(C)C)c3n2)CC1]

The following compounds may also be cited:

Compound Ii

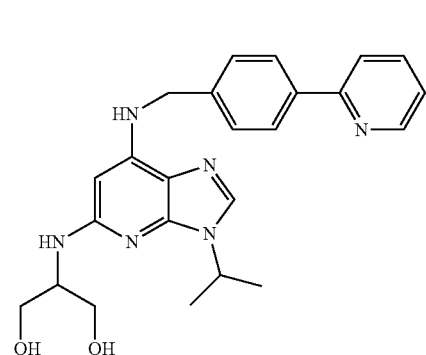

Compound Ij

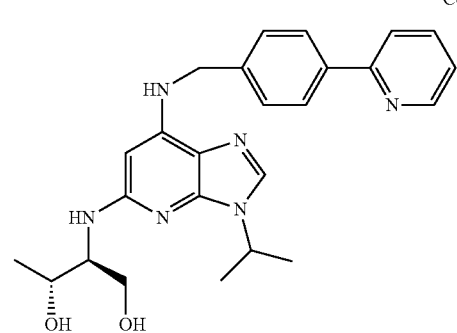

Compound Ik

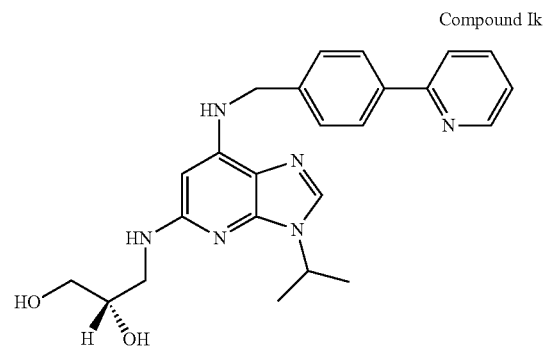

Compound Il

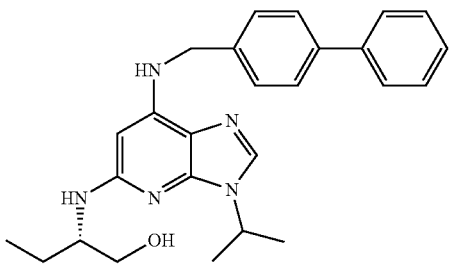

Compound Im

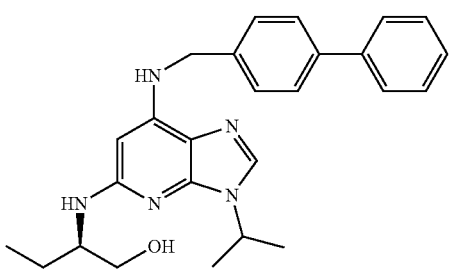

Compound In

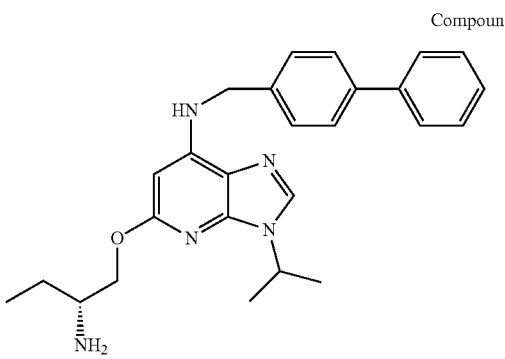

Compound Io

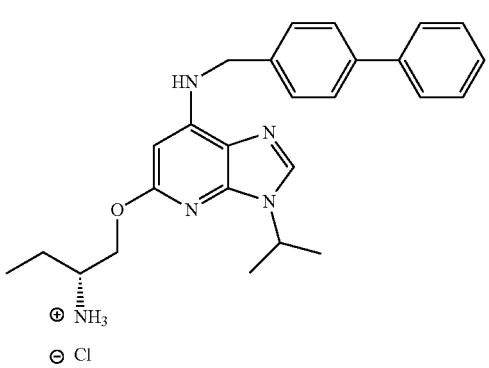

Compound Ip

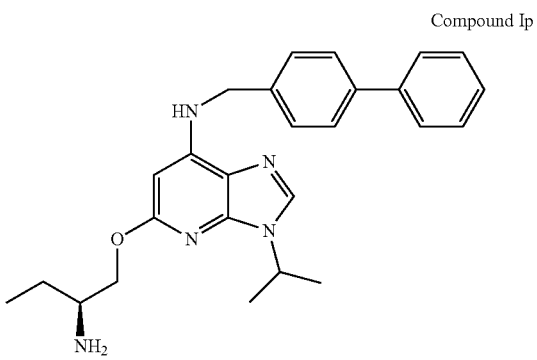

Iq

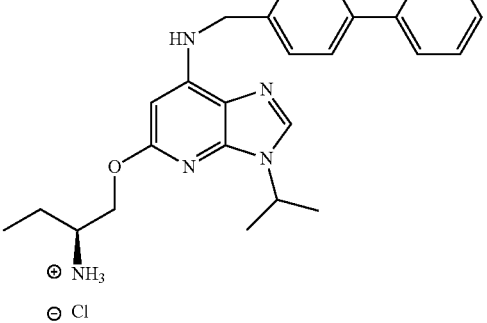

The stereoisomers, hydrates, and salts of each and all of the compounds of the invention cited above are also in the scope of the invention.

As it will be noted, in the compounds of Formulas Ia to Im, A is N.

In the compounds of formula In to Iq, A is O.

Other preferred compounds of the invention are those corresponding to the compounds of Formula Ia to Im, in which A is CH or A is O, The compounds of the invention may be manufactured by any appropriate process well-known from the man skilled in the art.

However when A is N, on the one hand, these compounds may not be prepared by the classical process of synthesis of 2,6,9-trisubstituted purines.

This classical process involves a step in which the 2-chlorine-substituted purine is heated in presence of an amino-alcohol for obtaining, for example, Roscovitine, at a temperature comprised between 145° C. and 170° C.

But when applying this process to the corresponding 3,5,7-trisubstituted imidazo[4,5-b]pyridine, no reaction occurred.

When rising the temperature, only degradation products were obtained.

On the other hand, applying the classical process for preparing deazapurine was also found not appropriate.

Indeed, this classical process described by Francis, J E and Moskal, M A in Can J Chem 1992, 70 pages 1288-1295, first involves the formation on an amidine by reaction of a secondary amide with a aminocyanoimidazole using phosphoryl chloride as reagent. In a second step, the amidine is cyclised into the imidazopyridine using NaH as base. This process could not be applied to prepare the compounds object of the present invention as it only affords derivatives bearing an unsubstituted amino group in position 7. Further when substituents contain hydroxyl groups they should be protected during the formation of the heterocycle. In another synthesis described by Koch, M in WO 2006/027366, the nature of the substituent than can be introduced in position 5 is limited as formed from a nitroso group and by the same process, only the unsubstituted 7-amino group is described.

To palliate the drawbacks of the processes of the prior art, the invention proposes an original and versatile process in which the compounds of the following formula II are used:

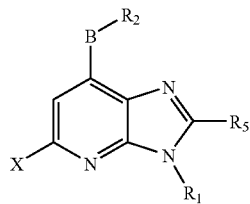

Formula II wherein:
B is O or S or NH or a halogen atom,
$R_1$ is:
 a $C_1$-$C_6$ alkyl group optionally branched and/or optionally substituted by one or more hydroxy groups, or
 a $C_3$-$C_6$ cycloalkyl group optionally substituted by one or more hydroxy groups, or
 an aryl group optionally substituted by one or more halogen atoms, and/or hydroxy groups, and/or $C_1$-$C_3$ alkyloxy groups, and/or optionally containing one or more heteroatoms, or
 a $C_1$-$C_5$ alkylaryl group, the aryl group being optionally substituted by one or more halogen atoms, and/or hydroxy groups, and/or $C_1$-$C_3$ alkyl groups, and/or $C_1$-$C_3$ alkyloxy groups, and/or optionally containing one or more heteroatoms,
$R_2$ is:
 an aryl group optionally substituted by one or more halogen atoms, and/or hydroxy groups, and/or $C_1$-$C_3$ alkyloxy groups, and/or carboxylic acid groups, and/or carboxylic ester groups, and/or amine groups, and/or $CF_3$ groups, and/or optionally containing one or more heteroatoms, thus creating a 2-pyridyl group, or a 3-pyridyl group, or a 4-pyridyl group, or a 2-thienyl or a 3-thienyl group, or
 a methylbiaryl group, wherein each aryl cycle is optionally substituted by one or more halogen atoms, and/or hydroxy groups, and/or $C_1$-$C_3$ alkyloxy groups, and/or $CF_3$ groups, and/or carboxylic acid groups, and/or carboxylic ester groups, and/or amine groups, and/or optionally containing one or more heteroatoms, or
 a methylaryl group, the aryl cycle being optionally substituted by one or more halogen atoms, and/or hydroxy groups, and/or $C_1$-$C_3$ alkyloxy groups, and/or $CF_3$ groups, and/or optionally containing one or more heteroatoms, thus creating a 2-pyridyl group, or a 3-pyridyl group, or a 4-pyridyl group, or a 2-thienyl group or a 3-thienyl group,
 a biaryl group, each aryl cycle optionally containing one or more heteroatoms thus creating a 2-pyridyl group, or a 3-pyridyl group, or a 4-pyridyl group, or a 2-thienyl group or a 3-thienyl group, or each aryl cycle is optionally substituted by one or more halogen atoms, and/or hydroxy groups, and/or $C_1$-$C_3$ alkyloxy groups, and/or $CF_3$ groups, and/or carboxylic acid groups, and/or carboxylic ester groups, and/or amine groups,
 or B and $R_2$ together form a non aromatic cycle,
$R_5$ is:
 a halogen atom, or
 a hydrogen atom, or
 a $C_1$-$C_5$ alkyl group optionally substituted by one or more hydroxy groups and/or amine groups and/or halogen atoms and/or carboxylic acid groups, or
 a $(C_1$-$C_4)$alkyl$(C_3$-$C_6)$cycloalkyl group in which the cycloalkyl group is optionally substituted by one or more hydroxy groups and/or amine groups and/or halogen atoms and/or carboxylic acid groups,
X is Cl or Br or I or $NH_2$.
These compounds of formula II are also in the scope of the invention.
Preferred compounds of Formula II are those in which X is I,
Thus, the invention also proposes a process for manufacturing compounds of the following formula I:

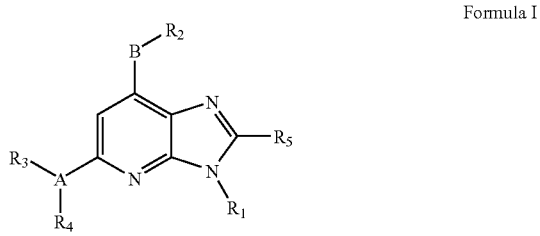

Formula I wherein:
A is N,
$R_3$ is:
 H, or
 a $C_1$-$C_5$ alkyl group, or
 =O, or
 a $(C_1$-$C_3)$ alkyl-C=O group in which the alkyl is optionally substituted by one or more halogen atoms, and/or hydroxy groups, and/or amino groups, and/or alkyloxy groups, and/or ketone groups,
$R_4$ is:
 H, or
 a $C_1$-$C_6$ alkyl group optionally substituted by one or more halogen atoms, and/or hydroxy groups, and/or amino groups, and/or alkyloxy groups, and/or ketone groups,
 a $C_3$-$C_6$ cycloalkyl group optionally substituted by one or more halogen atoms, and/or hydroxy groups, and/or amino groups, and/or alkyloxy groups, and/or ketone groups, or
 a $(C_j$—$C_5)$alkyl$(C_3$-$C_6)$cycloalkyl group optionally substituted by one or more halogen atoms, and/or hydroxy groups, and/or amino groups, and/or alkyloxy groups, and/or ketone groups, or
 =O, or
 O=CCF$_3$, or
 a $C_1$-$C_6$ alkyl group substituted by an ester group such as a O-acyl group, or an amino acyl group derived from natural, or non natural amino acids, or an acetyl group or a nicotinyl group,
or A, $R_3$ and $R_4$ together form a $C_5$-$C_7$ cycloalkyl group, optionally containing one or more heteroatoms, preferably a piperazine group,
B is O or S or NH or a halogen atom,
$R_1$ is:
 a $C_1$-$C_6$ alkyl group optionally substituted by one or more hydroxy groups, or
 a $C_3$-$C_6$ cycloalkyl group optionally substituted by one or more hydroxy groups, or
 an aryl group optionally substituted by one or more halogen atoms, and/or hydroxy groups, and/or $C_1$-$C_3$ alkyloxy groups, and/or optionally containing one or more heteroatoms, or
 a $C_1$-$C_5$ alkylaryl group, the aryl group being optionally substituted by one or more halogen atoms, and/or hydroxy groups, and/or $C_1$-$C_3$ alkyl groups, and/or $C_1$-$C_3$ alkyloxy groups, and/or optionally containing one or more heteroatoms, $R_2$ is:
- an aryl group optionally substituted by one or more halogen atoms, and/or hydroxy groups, and/or $C_1$-$C_3$ alkyloxy groups, and/or carboxylic acid groups, and/or carboxylic ester groups, and/or amine groups, and/or $CF_3$ groups, and/or optionally containing one or more heteroatoms, thus creating a 2-pyridyl group, or a 3-pyridyl group, or a 4-pyridyl group, or a 2-thienyl or a 3-thienyl group, or
- a methylbiaryl group, wherein each aryl cycle is optionally substituted by one or more halogen atoms, and/or hydroxy groups, and/or $C_1$-$C_3$ alkyloxy groups, and/or $CF_3$ groups, and/or carboxylic acid groups, and/or carboxylic ester groups, and/or amine groups, and/or optionally containing one or more heteroatoms, or
- a methylaryl group, the aryl ring being optionally substituted by one or more halogen atoms, and/or hydroxy groups, and/or $C_1$-$C_3$ alkyloxy groups, and/or $CF_3$ groups, and/or optionally containing one or more heteroatoms, thus creating a 2-pyridyl group, or a 3-pyridyl group, or a 4-pyridyl group, or a 2-thienyl group or a 3-thienyl group,
- a biaryl group, each aryl cycle optionally containing one or more heteroatoms thus creating a 2-pyridyl group, or a 3-pyridyl group, or a 4-pyridyl group, or a 2-thienyl group or a 3-thienyl group, or each aryl cycle is optionally substituted by one or more halogen atoms, and/or hydroxy groups, and/or $C_1$-$C_3$ alkyloxy groups, and/or $CF_3$ groups, and/or carboxylic acid groups, and/or carboxylic ester groups, and/or amine groups, or B and $R_2$ together form a non aromatic cycle, $R_5$ is:
- a halogen atom, or
- a hydrogen atom, or
- a $C_1$-$C_5$ alkyl group optionally substituted by one or more hydroxy groups and/or amine groups and/or halogen atoms and/or carboxylic acid groups, or
- a ($C_1$-$C_4$)alkyl($C_3$-$C_6$)cycloalkyl group in which the cycloalkyl group is optionally substituted by one or more hydroxy groups and/or amine groups and/or halogen atoms and/or carboxylic acid groups, and the salts, hydrates, and stereoisomers thereof, comprising a step of reaction of a compound of the following formula II:

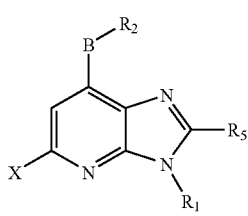

Formula II wherein B, $R_2$, $R_1$ and $R_5$ are as defined above for the compounds of formula I and X is Br, Cl, I or $NH_2$.

In a first embodiment of the process of the invention, this step of reaction is a step of coupling the compounds of Formula II in which X is Cl, Br or I with a compound of the following Formula III:

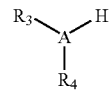

Formula III wherein A, $R_3$ and $R_4$ are as defined for Formula I, in presence of a catalyst selected from $Pd(OAc)_2$, tris(dibenzylidenacetone)dipalladium also called, $Pd_2 dba_3$ or CuI, and optionally in presence of a ligand such as 2,2'-bis(diphenylphosphino)-1,1-binaphtyl also called Binap or ethyleneglycol or a diketone.

In a second embodiment of the process of the invention, this step of reaction is a step of coupling a compound of Formula II in which X is $NH_2$ with a compound of the following Formula IV:

Y—$R_5$          Formula IV in which Y is I, Br or $C_1$ and $R_6$ is $R_3$ or $R_4$, for obtaining a compound of the following formula V:

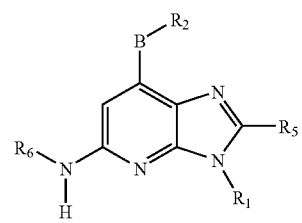

Formula V and when $R_3$ and $R_4$ are different from H, followed by a step of coupling the compound of Formula V with a compound of the following Formula VI:

Y—$R_7$          Formula VI in which Y is I, Br or $C_1$ and $R_7$ is $R_3$ when $R_6$ is $R_4$ or $R_7$ is $R_4$ when $R_6$ is $R_3$, said coupling steps being carried out in basic conditions.

In all the embodiments of the process of the invention, preferably, X and Y are I or Br, more preferably I, in each occurrence.

The invention also proposes a compound according to the invention or obtained by the process of the invention for use as medicament.

Another object of the invention is a pharmaceutical composition comprising at least one compound of the invention, or obtained by the process of the invention, and at least one pharmaceutically acceptable excipient.

A further object of the invention is the use of at least one compound of the invention, or obtained by the process of the invention, in the manufacture of a medicament for the treatment of a disease due to an abnormal proliferation of cells, either tumoral or non-tumoral by nature.

In one embodiment of said use according to the invention, said disease is a tumor, such as a solid tumor, metastatic or not, or leukemia.

In another embodiment, said disease is a neurodegenerative disease involving abnormal activity of CDK5 and/or CDK1.

More particularly, said neurodegenerative disease is Parkinson's disease.

But, said neurodegenerative disease may also be Alzheimer's disease and related Taupathies.

In still another embodiment, said disease is a viral disease, such as HIV, Herpes, cytomegalovirus, etc. . . . .

Also, the invention encompasses the use of at least one compound of the invention, or obtained by the process of the invention, in the manufacture of a medicament for the treatment of pain.

Furthermore, at least one compound of the invention, or obtained by the process of the invention, is advantageously used in the manufacture of a medicament or in a method of treatment of renal diseases such as mesangial proliferative glomerulonephritis, crescentic glomerulonephritis, collapsing glomerulopathy, proliferative lupus nephritis, polycystic kidney diseases, diabetic nephropathy, acute kidney injury and cisplatin-induced nephrotoxicity.

But, at least one compound of the invention or at least one compound obtained by the process of the invention is also of interest in the manufacture of a medicament and/or a method of treatment of inflammations such as pleural inflammation, arthritis, cystic fibrosis or glaucomas Finally compounds of the invention are also of interest to enhance insulin production by the pancreas in the case of type 2 diabetes.

In all the embodiments and variations of the use of at least one compound of the invention or the corresponding method of treatment, preferably, said at least one compound has the following formula Ia:

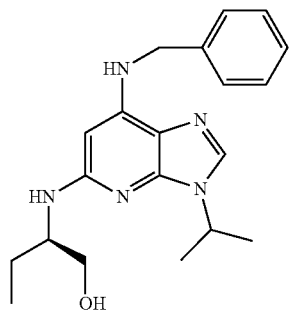

Formula Ia

More preferably, said at least one compound is the compound of the following formula Ib:

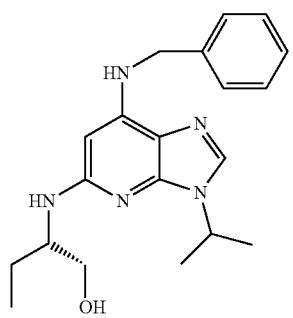

Formula Ib

But in another preferred variation said at least one compound is the compound of the following formula Ic:

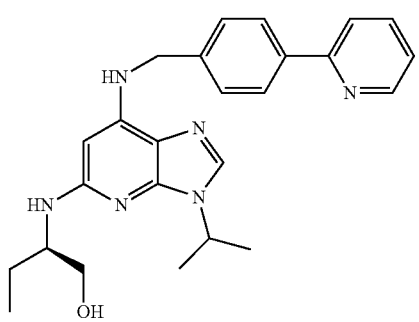

Formula Ic

However in another preferred variation of the use of at least one compound of the invention, said at least one compound is the compound of the following formula Id:

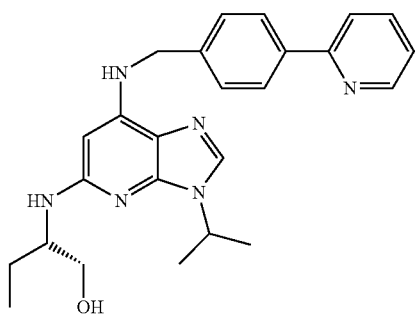

Formula Id

In another variation of the use of at least one compound of the invention, said at least one compound is the compound of the following formula Ie:

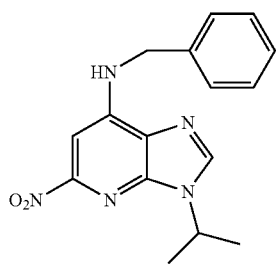

Formula Ie

But, said at least one compound may also be the compound of the following formula If:

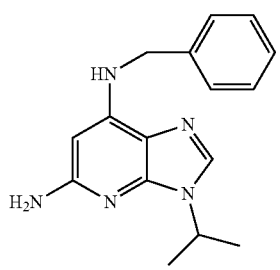

Formula If

But, said at least one compound may also be the compound of the following formula Ig:

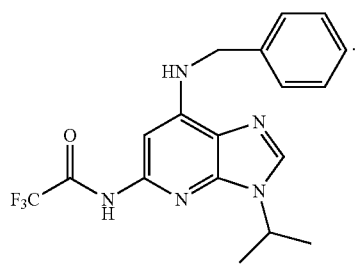

Formula Ig

Furthermore, said at least one compound may also be the compound of the following formula Ih:

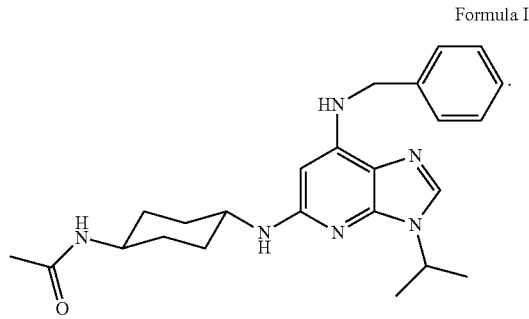

Formula Ih

The salts, hydrates and stereoisomers of the compounds of formula Ia to Ih may also be used as the at least one compound.

Compounds Ii to Iq as described above are also of course well appropriate to be implemented for the claimed uses and methods of treatment.

Figure 2:
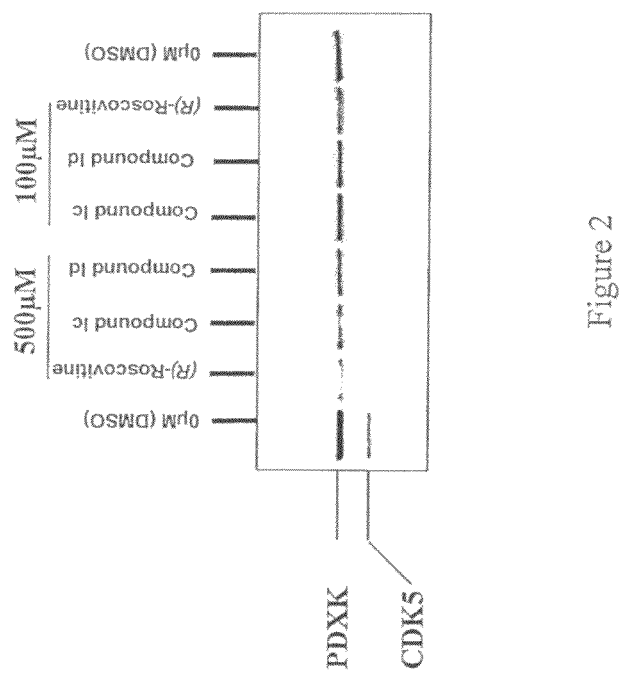
Figure 3:
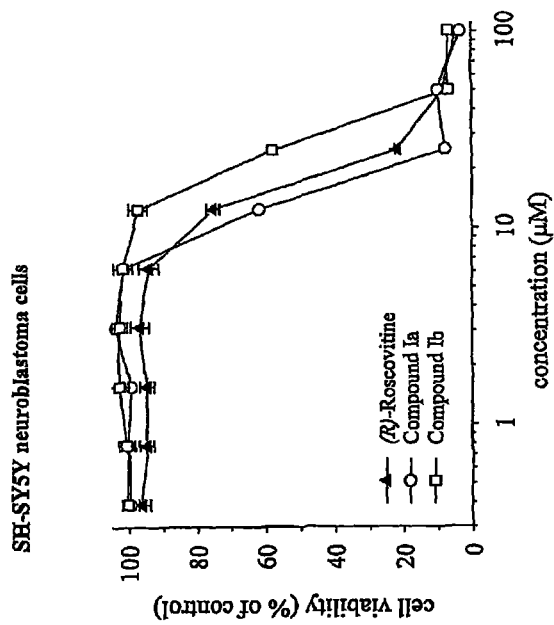
Figure 4:
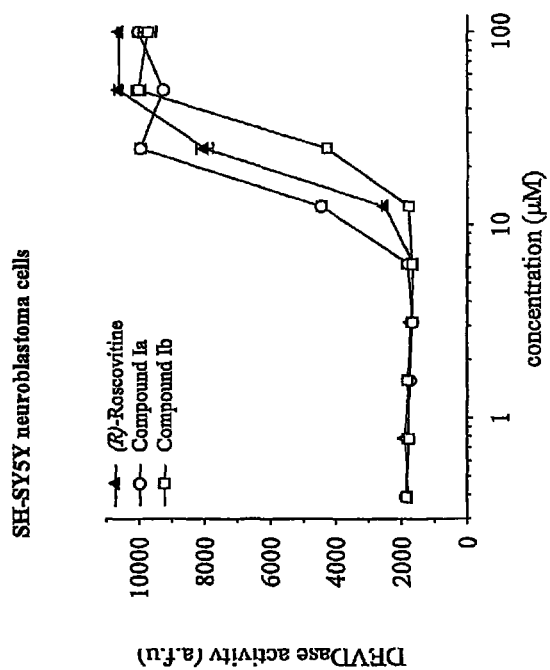
Figure 5:
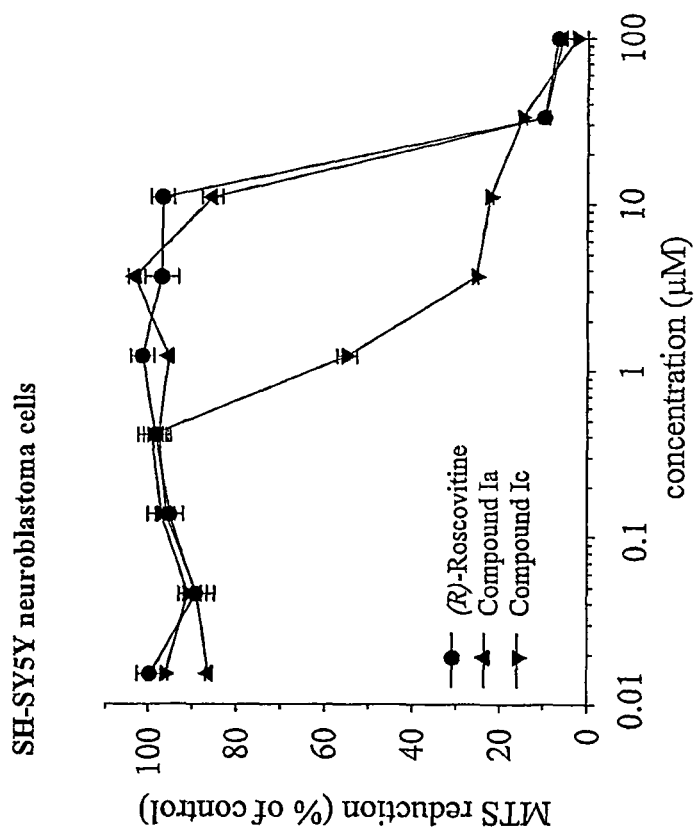
Figure 6:
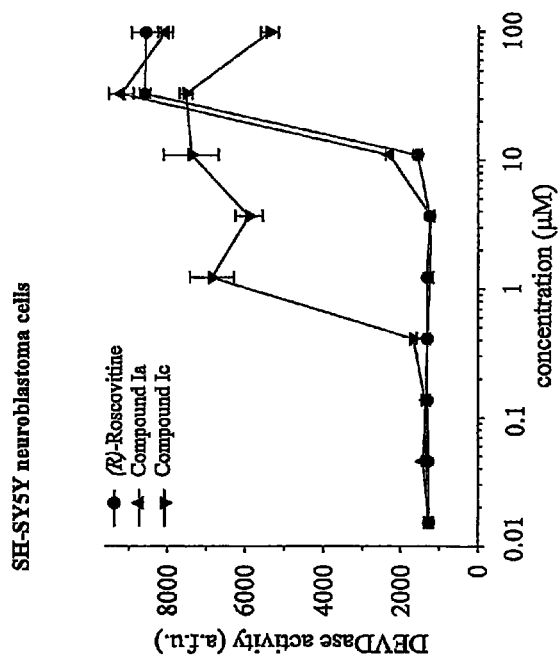
Figure 7:
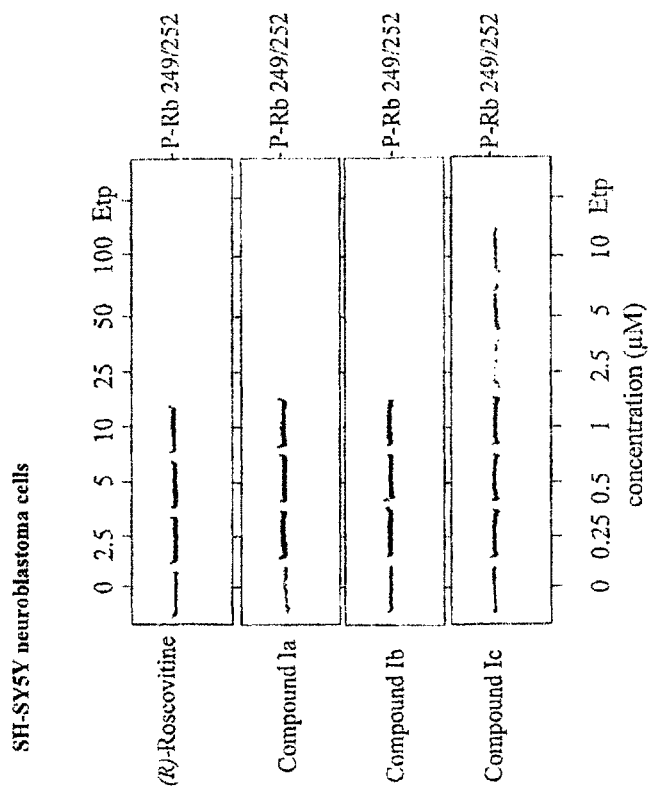
Figure 8:
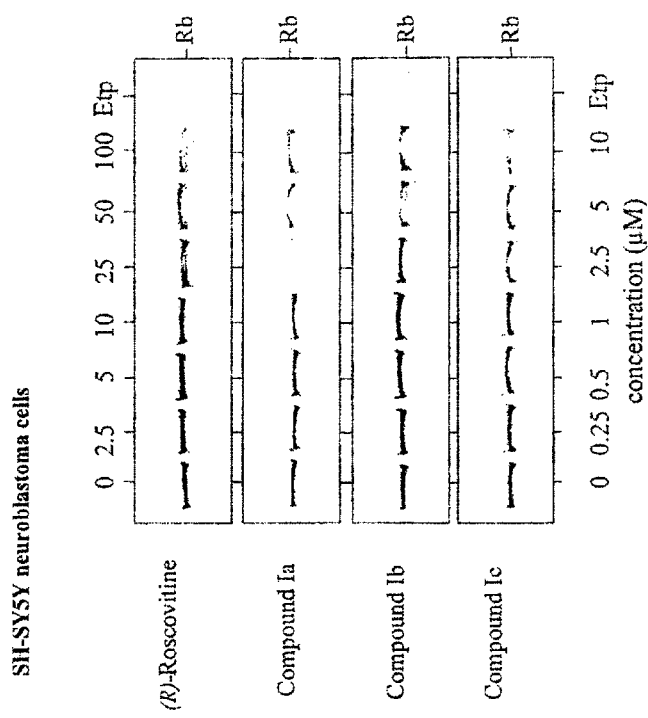
Figure 9:
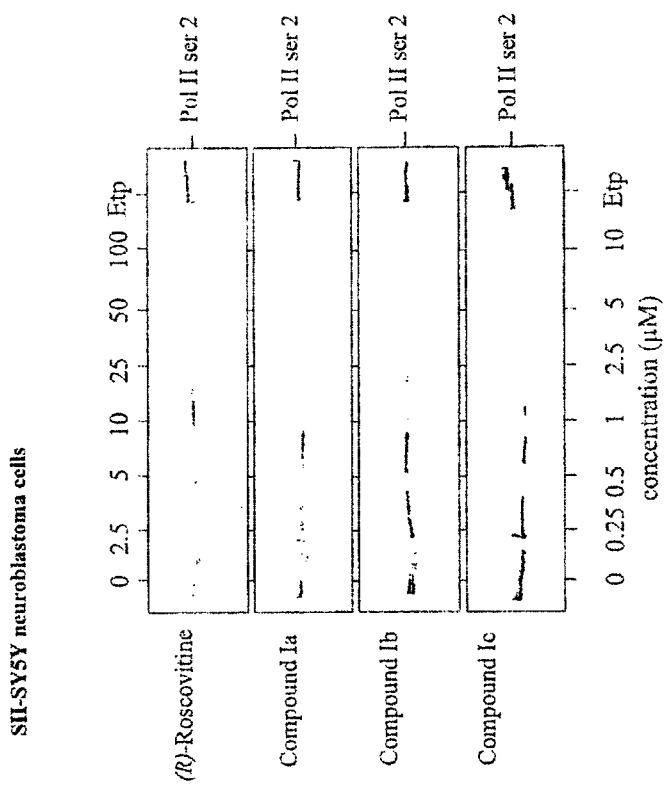
Figure 10:
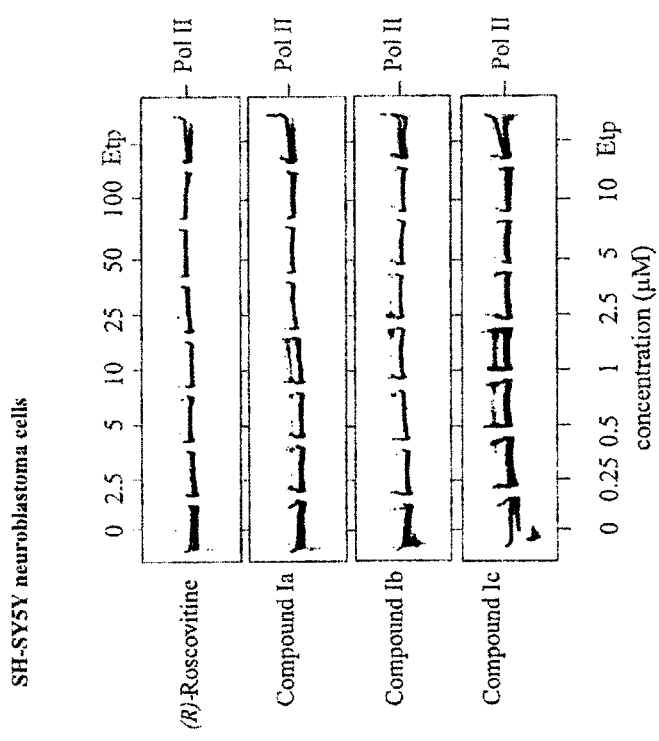
Figure 11:
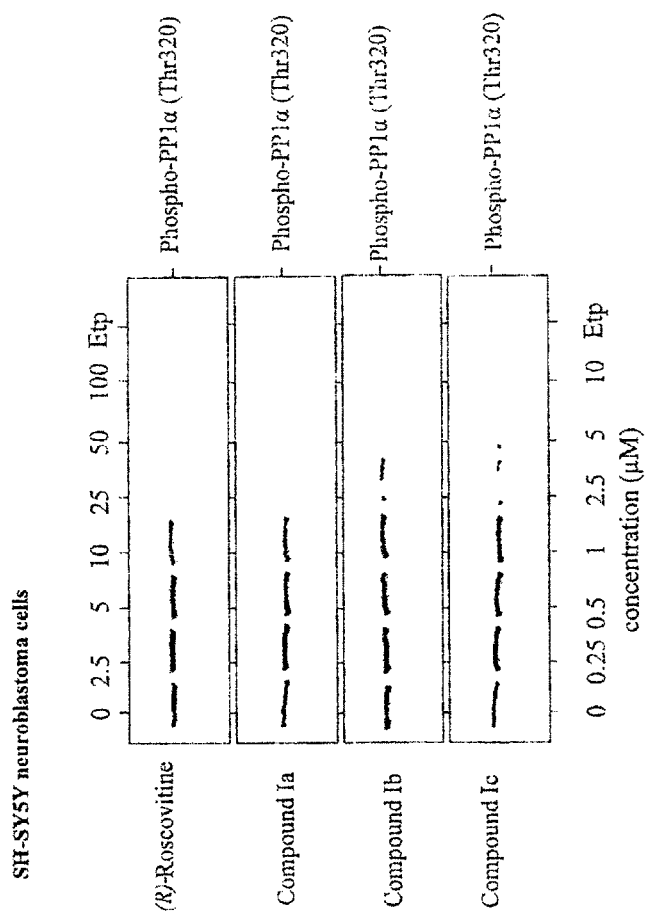
Figure 12:
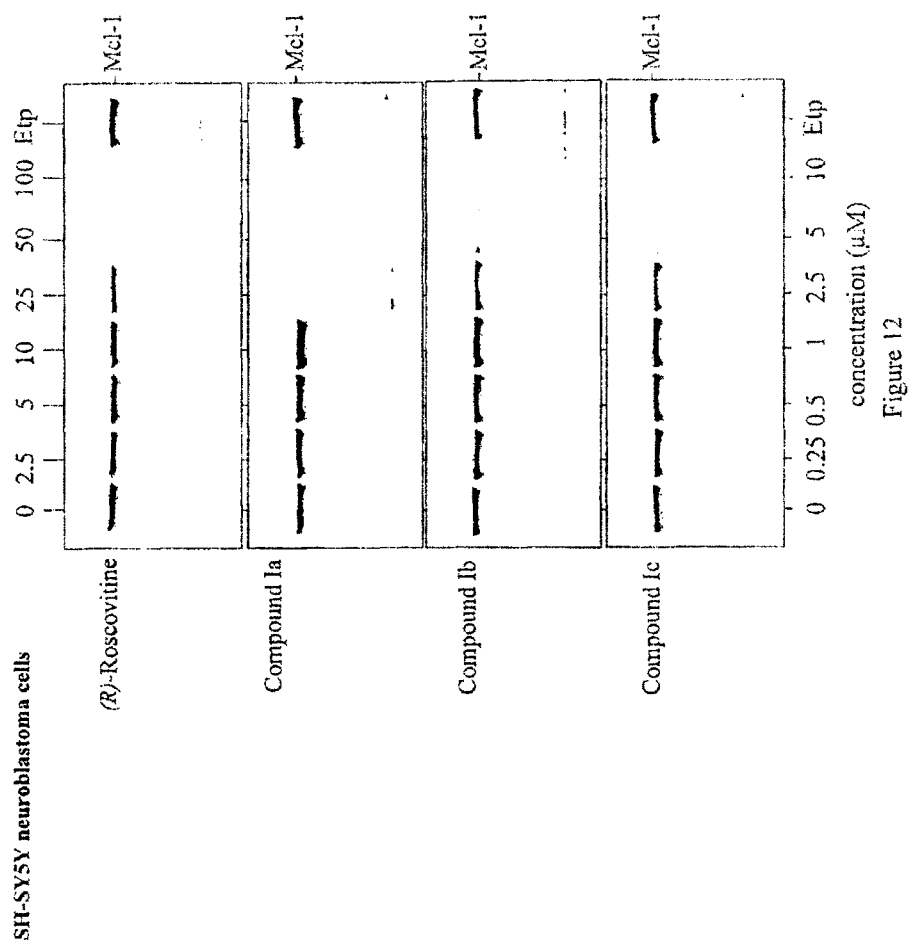
Figure 13:
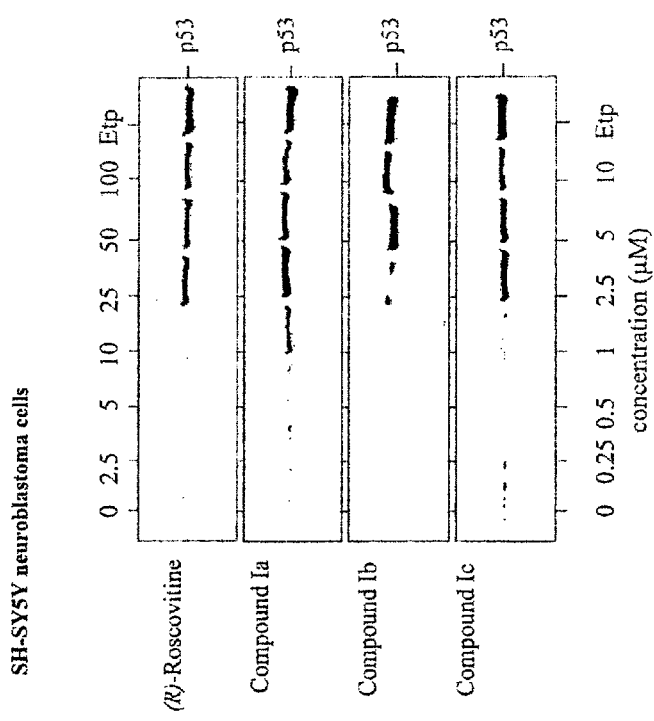
Figure 14:
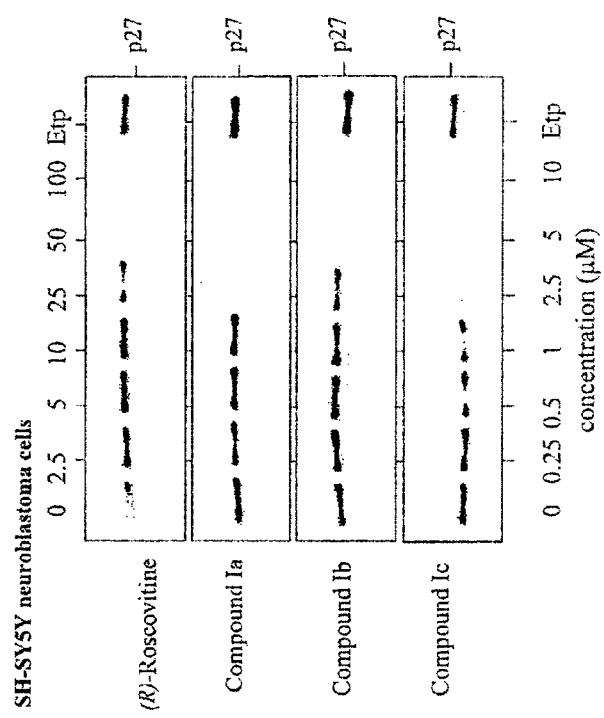
Figure 15:
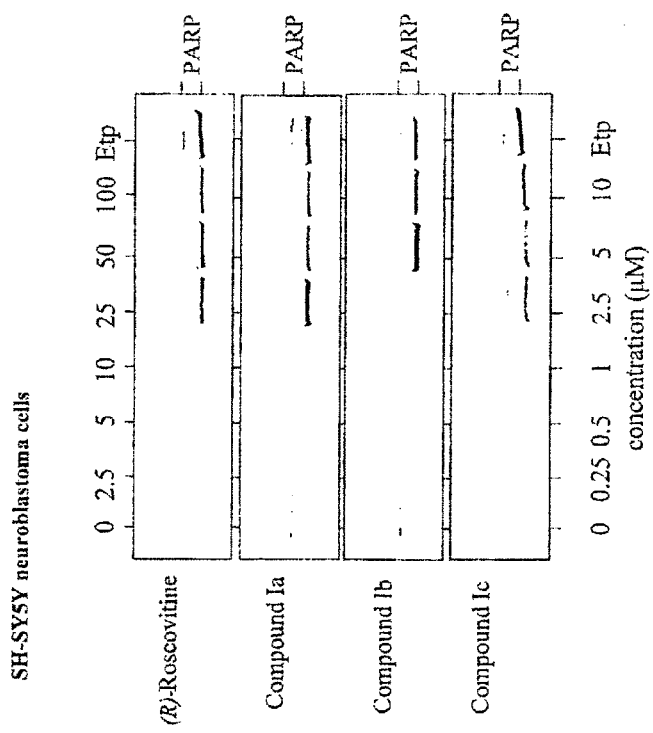
Figure 16:
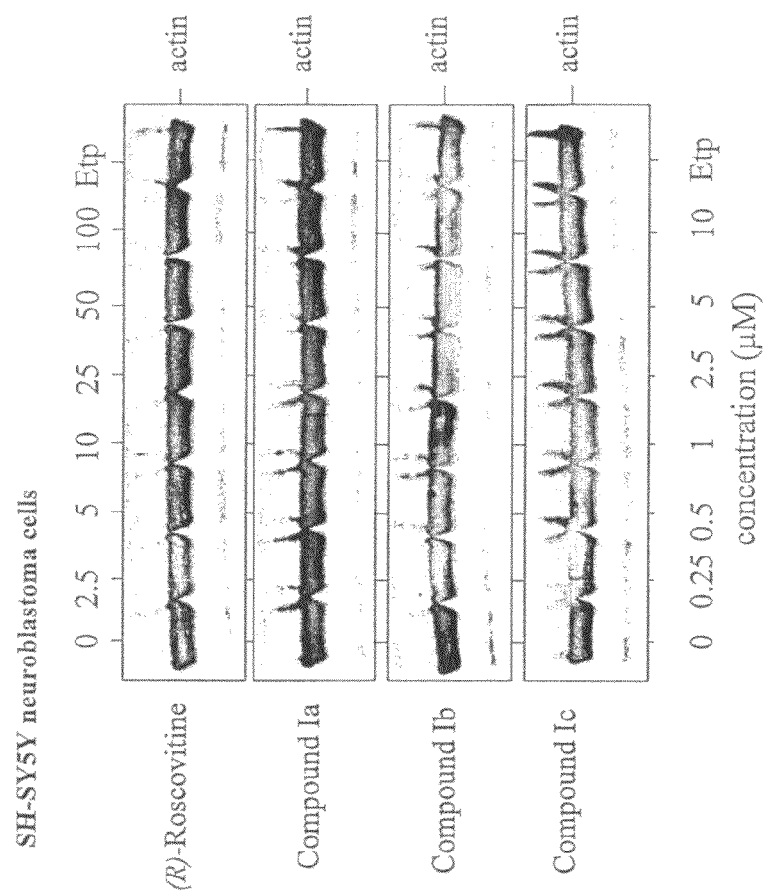

The invention will be better understood and further features and advantages thereof will become apparent when reading the description which follows, which is made in a reference to examples which are only illustrative and which do not limit the scope of the invention and in reference to the figures in which:

FIG. 1 shows the results of the silver staining assay carried out with 500 μM or 100 μM, respectively, of (R)-Roscovitine, or of the compound of Formula Ic, or of the compound of Formula Id, for determining the interaction of the compounds of the invention and Roscovitine with pyridoxal kinase, FIG. 2 shows an immunoblot corresponding to FIG. 1 for showing the effect of (R)-Roscovitine, of the compound of Formula Ic, and of the compound of Formula Id, at a concentration of 500 μM and 100 μM, on kinase PDXK and CDK5, FIG. 3 shows the effects of (R)-Roscovitine, of the compound of Formula Ia, and of the compound of Formula Ib, at different concentrations, on the cell viability of SH-SY5Y neuroblatoma cells, FIG. 4 shows the effects of (R)-Roscovitine, of the compound of Formula Ia, and the of compound of Formula Ib, at different concentrations, on caspases activity (DEVDase) measured in arbitrary fluorescent units (a.f.u.) of SH-SY5Y neuroblastome cells, FIG. 5 shows the effects of different concentrations of (R)-Roscovitine, of the compound of Formula Ia, and of the compound of Formula Ic, on the MTS reduction of SH-SY5Y neuroblastoma cells, FIG. 6 shows the effects of different concentrations of (R)-Roscovitine, of the compound of Formula Ia, and of the compound of Formula Ic, on capases activity (DEVDase activity) expressed in arbitrary fluorescent units (a.f.u), of SH-SY5Y neuroblastoma cells, FIG. 7 shows the effects of (R)-Roscovitine, of the compound of Formula Ia, of the compound of Formula Ib, and of the compound of Formula Ic, at different concentrations, on retinoblastoma protein phosphorylation of SH-SY5Y neuroblastoma cells. In this Figure, the upper scale applies to (R)-Roscovitine, the compounds of Formula Ia and of Formula Ib, and the lower scale applies to the compound of Formula Ic, FIG. 8 shows the effects of (R)-Roscovitine, of the compound of Formula Ia, of the compound of Formula Ib, and of the compound of Formula Ic, at different concentrations, on retinoblastoma total protein of SH-SY5Y neuroblastoma cells. In this Figure, the upper scale applies to (R)-Roscovitine, the compounds of Formula Ia and of Formula Ib, and the lower scale applies to the compound of Formula Ic, FIG. 9 shows the effects of (R)-Roscovitine, of the compound of Formula Ia, of the compound of Formula Ib, and of the compound of Formula Ic, at different concentrations, on RNA polymerase II Ser2 phosphorylation of SH-SY5Y neuroblastoma cells. In this Figure, the upper scale applies to (R)-Roscovitine, the compounds of Formula Ia and of Formula Ib, and the lower scale applies to the compound of Formula Ic, FIG. 10 shows the effects of (R)-Roscovitine, of the compound of Formula Ia, of the compound of Formula Ib, and of the compound of Formula Ic, at different concentrations, on RNA polymerase II total protein of SH-SY5Y neuroblastoma cells. In this Figure, the upper scale applies to (R)-Roscovitine, the compounds of Formula Ia and of Formula Ib, and the lower scale applies to the compound of Formula Ic, FIG. 11 shows the effects of (R)-Roscovitine, of the compound of Formula Ia, of the compound of Formula Ib, and of the compound of Formula Ic, at different concentrations, on protein phosphatase1-alpha phosphorylation on Thr320 of SW SY5Y neuroblastoma cells. In this Figure, the upper scale applies to (R)-Roscovitine, the compounds of Formula Ia and of Formula Ib, and the lower scale applies to the compound of Formula Ic, FIG. 12 shows the effects of (R)-Roscovitine, of the compound of Formula Ia, of the compound of Formula Ib, and of the compound of Formula Ic, at different concentrations, on Mcl-1 survival factor of SH-SY5Y neuroblastoma cells. In this Figure, the upper scale applies to (R)-Roscovitine, the compounds of Formula Ia and of Formula Ib, and the lower scale applies to the compound of Formula Ic, FIG. 13 shows the effects of (R)-Roscovitine, of the compound of Formula Ia, of the compound of Formula Ib, and of the compound of Formula Ic, at different concentrations, on p53 total protein levels of SH-SY5Y neuroblastoma cells. In this Figure, the upper scale applies to (R)-Roscovitine, the compounds of Formula Ia and of Formula Ib, and the lower scale applies to the compound of Formula Ic, FIG. 14 shows the effects of (R)-Roscovitine, of the compound of Formula Ia, of the compound of Formula Ib, and of the compound of Formula Ic, at different concentrations, on p27 total protein levels of SH-SY5Y neuroblastoma cells. In this Figure, the upper scale applies to (R)-Roscovitine, the compounds of Formula Ia and of Formula Ib, and the lower scale applies to the compound of Formula Ic, FIG. 15 shows the effects of (R)-Roscovitine, of the compound of Formula Ia, of the compound of Formula Ib, and of the compound of Formula Ic, at different concentrations, on PARP cleavage SH-SY5Y neuroblastoma cells. In this Figure, the upper scale applies to (R)-Roscovitine, the compounds of Formula Ia and of Formula Ib, and the lower scale applies to the compound of Formula Ic, and FIG. 16 shows the effects of (R)-Roscovitine, of the compound of Formula Ia, of the compound of Formula Ib, and of the compound of Formula Ic, at different concentrations, on actin total protein of SH-SY5Y neuroblastoma cells, as loading control for FIGS. 5 to 14. In this FIG. 16, the upper scale applies to (R)-Roscovitine, the compounds of Formula Ia and of Formula Ib, and the lower scale applies to the compound of Formula Ic.

The compounds of the invention have a structure which is close to the structure of Roscovitine but they are deazapurines.

More precisely, the compounds of the invention have the following formula I:

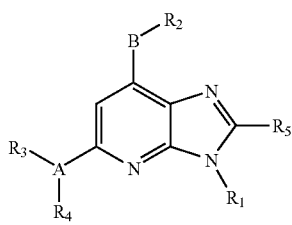

Formula I wherein:
A is CH or N or O,
$R_3$ is:
  H, or
  a $C_1$-$C_5$ alkyl group, or
  =O, or
  a ($C_1$-$C_3$) alkyl-C=O group in which the alkyl is optionally substituted by one or more halogen atoms, and/or hydroxy groups, and/or amino groups, and/or alkyloxy groups, and/or ketone groups,
$R_4$ is:
  H, or
  a $C_1$-$C_6$ alkyl group optionally substituted by one or more halogen atoms, and/or hydroxy groups, and/or amino groups, and/or alkyloxy groups, and/or ketone groups,
  a $C_3$-$C_6$ cycloalkyl group optionally substituted by one or more halogen atoms, and/or hydroxy groups, and/or amino groups, and/or alkyloxy groups, and/or ketone groups, or
  a ($C_1$-$C_5$)alkyl($C_3$-$C_6$)cycloalkyl group optionally substituted by one or more halogen atoms, and/or hydroxy groups, and/or amino groups, and/or alkyloxy groups, and/or ketone groups, or
  =O, or
  O=CCF$_3$, or
  a $C_1$-$C_6$ alkyl group substituted by an ester group such as a O-acyl group, or an amino acyl group derived from natural, or non natural amino acids, or an acetyl group or a nicotynyl group,
or A, $R_3$ and $R_4$ together form a $C_5$-$C_7$ cycloalkyl group, optionally containing one or more heteroatoms, preferably a piperazine group,
B is O or S or NH or a halogen atom,
$R_1$ is:
  a $C_1$-$C_6$ alkyl group optionally substituted by one or more hydroxy groups, or
  a $C_3$-$C_6$ cycloalkyl group optionally substituted by one or more hydroxy groups, or
  an aryl group optionally substituted by one or more halogen atoms, and/or hydroxy groups, and/or $C_1$-$C_3$ alkyloxy groups, and/or optionally containing one or more heteroatoms, or
  a $C_1$-$C_5$ alkylaryl group, the aryl group being optionally substituted by one or more halogen atoms, and/or hydroxy groups, and/or $C_1$-$C_3$ alkyl groups, and/or $C_1$-$C_3$ alkyloxy groups, and/or optionally containing one or more heteroatoms,
$R_2$ is:
  an aryl group optionally substituted by one or more halogen atoms, and/or hydroxy groups, and/or $C_1$-$C_3$ alkyloxy groups, and/or carboxylic acid groups, and/or carboxylic ester groups, and/or amine groups, and/or CF$_3$ groups, and/or optionally containing one or more heteroatoms, thus creating a 2-pyridyl group, or a 3-pyridyl group, or a 4-pyridyl group, or a 2-thienyl or a 3-thienyl group, or
  a methylbiaryl group, wherein each aryl cycle is optionally substituted by one or more halogen atoms, and/or hydroxy groups, and/or $C_1$-$C_3$ alkyloxy groups, and/or CF$_3$ groups, and/or carboxylic acid groups, and/or carboxylic ester groups, and/or amine groups, and/or optionally containing one or more heteroatoms, or
  a methylaryl group, the aryl cycle being optionally substituted by one or more halogen atoms, and/or hydroxy groups, and/or $C_1$-$C_3$ alkyloxy groups, and/or CF$_3$ groups, and/or optionally containing one or more heteroatoms, thus creating a 2-pyridyl group, or a 3-pyridyl group, or a 4-pyridyl group, or a 2-thienyl group or a 3-thienyl group,
  a biaryl group, each aryl cycle optionally containing one or more heteroatoms thus creating a 2-pyridyl group, or a 3-pyridyl group, or a 4-pyridyl group, or a 2-thienyl group or a 3-thienyl group, or each aryl cycle is optionally substituted by one or more halogen atoms, and/or hydroxy groups, and/or $C_1$-$C_3$ alkyloxy groups, and/or CF$_3$ groups, and/or carboxylic acid groups, and/or carboxylic ester groups, and/or amine groups,
or B and $R_2$ together form a non aromatic cycle,
$R_5$ is:
  a halogen atom, or
  a hydrogen atom, or
  a $C_1$-$C_5$ alkyl group optionally substituted by one or more hydroxy groups and/or amine groups and/or halogen atoms and/or carboxylic acid groups, or
  a ($C_1$-$C_4$)alkyl($C_3$-$C_6$)cycloalkyl group in which the cycloalkyl group is optionally substituted by one or more hydroxy groups and/or amine groups and/or halogen atoms and/or carboxylic acid groups,
and the salts, hydrates, and stereoisomers thereof.

Preferred substituents A, 13, and $R_1$ to $R_6$ in formula I as well as preferred compounds of that formula I have been previously defined.

The essential difference between Roscovitine and the compounds of formula I is the fact that the nitrogen in position 7 in the core of Roscovitine is replaced by a carbon in the compounds of formula I.

Otherwise stated, the pyrimidine cycle in the core of Roscovitine is replaced by a pydirine cycle in the compounds of the invention.

This difference is the key feature of the compounds of the invention which gives to the compounds of the invention their unique properties: they have less interaction with pyridoxal kinase than the purine type compounds of the prior art as shown in FIG. 1.

Indeed, the interaction of the compounds of the invention with pyridoxal kinase has been determined by the following method: (silver staining assay)

1000 μg of porcine brain lysate (100 μl of lysate at 10 μg/μl) completed with 100 μM of Roscovitine, or 100 μM of the compound of formula Id, or 100 μM of the compound of formula Ie have been loaded on agarose beads and washed with the bead buffer (50 mM Tris pH 7.4, 5 mM NaF, 250 mM NaCl, 5 mM EDTA, 5 mM EGTA, 0.1% NP-40, 10 μg/ml of leupeptin, aprotinin and soybean trypsin inhibitor and 100 μM benzamidine)

The results of these tests are shown in FIG. 1.

As can be seen in FIG. 1, the compounds of the invention exhibit a competitor effect for CDK5, which demonstrates that they indeed have an interaction with that enzyme.

Roscovitine exhibited a competitor effect for secondary targets Erk2 and PDXK. In contrast, the compounds of the invention exhibited no or little competitor effect for pyridoxal kinase and Erk2, which demonstrates that these proteins are not or very weak targets for the compounds of the invention.

Otherwise stated, the compounds of the invention exhibit an increased specificity for CDKs as compared to Roscovitine.

In addition, compared to the purine derivatives, it was noticed that they were somewhat less inhibitory towards CDK9, a kinase that should not be inhibited due to its key role in the transcription.

Furthermore, the inventors have discovered that when, in formula I, B—$R_2$ is different from $NH_2$, or has a short length of chain, and preferably contains at least one aryl group, the effects of the compounds of formula I on cell survival are enhanced despite modest difference in their effects on CDKs, Furthermore subtle differences in their selectivity (reduced effect on CDK9) suggest that less non-specific effects can be expected from these molecules compared to their purine counterparts.

Thus, the compounds of the present invention are trisubstituted or tetrasubstituted imidazo[4,5-b]pyridines, i.e 1-deazapurines.

The compounds of the invention have been tested as to their effects on different CDKs and cell lines as compared to Roscovitine.

These tests and their results are reported hereinafter in the section entitled "Results".

Furthermore, for those compounds of the invention in which A is N, the inventors have discovered a particularly appropriate process for their manufacture.

This process is based on the use of an intermediate compound which has the following formula II:

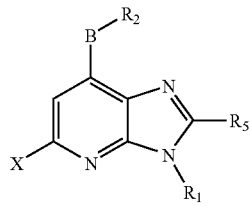

Formula II wherein:

B is O or S or NH $R_1$ is:
- a $C_1$-$C_6$ alkyl group optionally substituted by one or more hydroxy groups, or
- a $C_3$-$C_6$ cycloalkyl group optionally substituted by one or more hydroxy groups, or
- an aryl group optionally substituted by one or more halogen atoms, and/or hydroxy groups, and/or $C_1$-$C_3$ alkyloxy groups, and/or optionally containing one or more heteroatoms, or
- a $C_1$-$C_5$ alkylaryl group, the aryl group being optionally substituted by one or more halogen atoms, and/or hydroxy groups, and/or $C_1$-$C_3$ alkyl groups, and/or $C_1$-$C_3$ alkyloxy groups, and/or optionally containing one or more heteroatoms, $R_2$ is:
- an aryl group optionally substituted by one or more halogen atoms, and/or hydroxy groups, and/or $C_1$-$C_3$ alkyloxy groups, and/or carboxylic acid groups, and/or carboxylic ester groups, and/or amine groups, and/or $CF_3$ groups, and/or optionally containing one or more heteroatoms, thus creating a 2-pyridyl group, or a 3-pyridyl group, or a 4-pyridyl group, or a 2-thienyl or a 3-thienyl group, or
- a methylbiaryl group, wherein each aryl cycle is optionally substituted by one or more halogen atoms, and/or hydroxy groups, and/or $C_1$-$C_3$ alkyloxy groups, and/or $CF_3$ groups, and/or carboxylic acid groups, and/or carboxylic ester groups, and/or amine groups, and/or optionally containing one or more heteroatoms, or
- a methylaryl group, the aryl cycle being optionally substituted by one or more halogen atoms, and/or hydroxy groups, and/or $C_1$-$C_3$ alkyloxy groups, and/or $CF_3$ groups, and/or optionally containing one or more heteroatoms, thus creating a 2-pyridyl group, or a 3-pyridyl group, or a 4-pyridyl group, or a 2-thienyl group or a 3-thienyl group,
- a biaryl group, each aryl cycle optionally containing one or more heteroatoms thus creating a 2-pyridyl group, or a 3-pyridyl group, or a 4-pyridyl group, or a 2-thienyl group or a 3-thienyl group, or each aryl cycle is optionally substituted by one or more halogen atoms, and/or hydroxy groups, and/or $C_1$-$C_3$ alkyloxy groups, and/or $CF_3$ groups, and/or carboxylic acid groups, and/or carboxylic ester groups, and/or amine groups, or B and $R_2$ together form a non aromatic cycle, $R_5$ is:
- a halogen atom, or
- a hydrogen atom, or
- a $C_1$-$C_5$ alkyl group optionally substituted by one or more hydroxy groups and/or amine groups and/or halogen atoms and/or carboxylic acid groups, or
- a ($C_1$-$C_4$)alkyl($C_3$-$C_6$)cycloalkyl group in which the cycloalkyl group is optionally substituted by one or more hydroxy groups and/or amine groups and/or halogen atoms and/or carboxylic acid groups, X is Cl or Br or I or $NH_2$, These intermediate compounds are also in the scope of the invention.

Access to these compounds of Formula II is depicted in the following scheme 1.

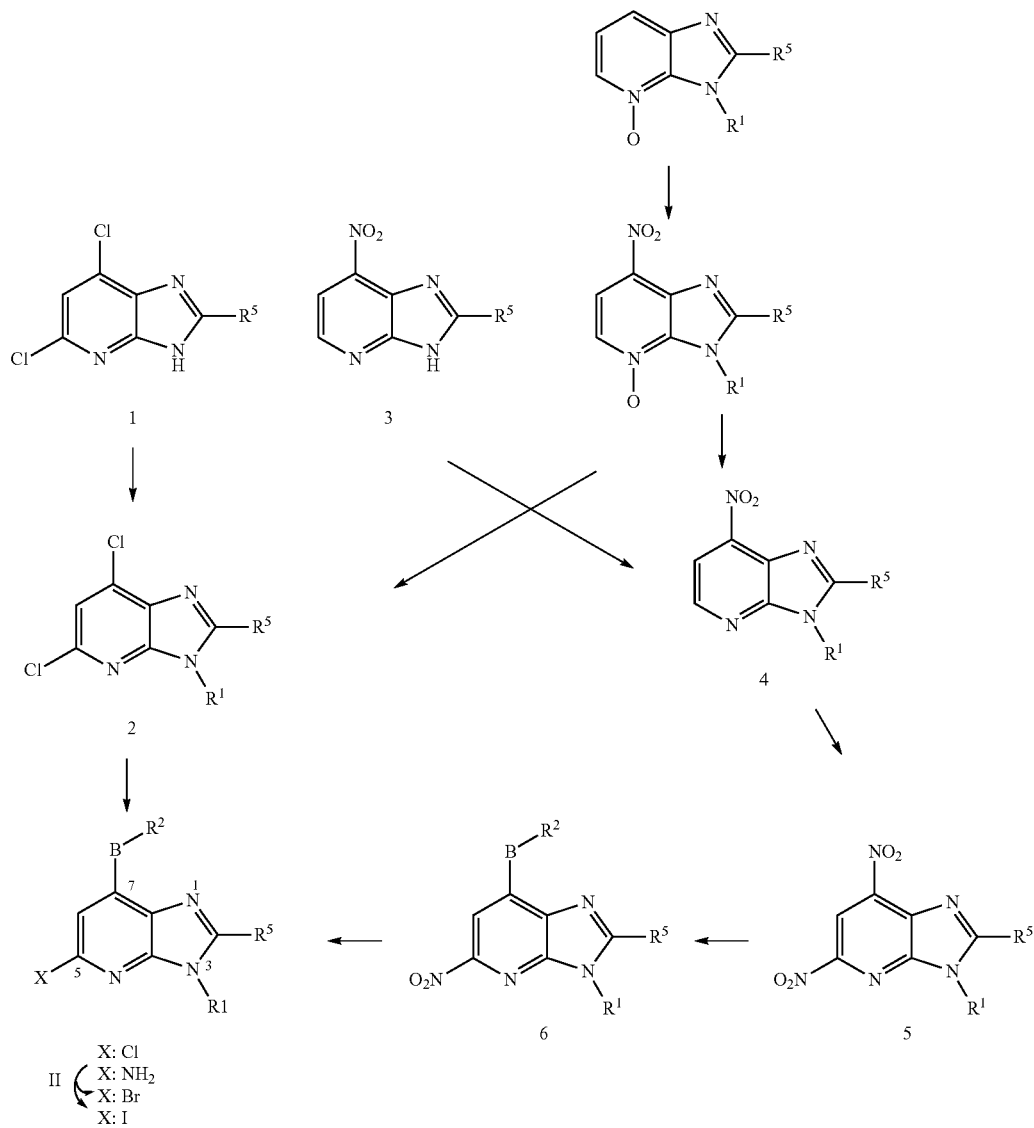

Three routes were used to prepare precursors of formula II:

Route a=5,7-dichloroimidazopyridine 1 obtained as described in G. Cristalli and al, "Nucleosides and nucleotides", 1985, 4, 625-639, was reacted with $R_1X$ (X=Br or I) in basic conditions to afford 2 which was further reacted with $R_2BH$ in butanol, using a tertiaryalkylamine (e.g $NEt_3$ or $NBu_3$) as base, at 90-100° C. to give IIa X=Cl.

Route b=Alkylation of 3 prepared according to known procedure in similar condition as for 1 led to 4 which is reacted with tetrabutylammonium nitrate to afford the dinitro compound 5. Reaction of S with $R_2BH$ in hot butanol or in DMF at 20-30° C. gave 6 which was reduced into III) X=$NH_2$ using Fe, HCl; IIb X=$NH_2$. IIb could be converted into either IIc X=Br or into IId when X=I. The conversion of IIb into IId was achieved upon heating in $CH_2I_2$ and an organic nitrite such as tert-butylnitrite or isopentylnitrite.

Route c=The third route is closely related to the second route. The alkylation step, that is to say the introduction of group R1 is performed earlier.

The process of manufacture of the compounds of Formula I makes use of the compounds of Formula II.

In a first embodiment, the process makes use of the compounds of Formula II in which X is Cl, Br or I, preferably I.

This process involves a step of coupling a compound of formula II with a nucleophile of the following formula III:

to afford a compound of formula I.

The coupling procedure uses a metal catalyst such as Pd(OAc)$_2$, Pd$_2$dba$_3$ or CuI in basic conditions, The base can be a carbonate such as Cs$_2$CO$_3$, a metal alcoholate such as tert-butylOK or tert-butylONa.

The metal catalysts are in most cases used with added ligands such as (±)Binap, Xantphos, or ethylene glycol or diketones. Examples of diketones ligands are described by Shafir et al in J. Amer. Chem. Soc. 2006, 126, 8742-8743 and Shafir, J. Amer. Chem. Soc 2007, 129, 3490-3491.

But, in a second embodiment, the process of the invention makes use of formula I in which X is NH$_2$.

In this second embodiment, one or two coupling steps are to be performed depending on the nature of the wanted substituent R$_3$ and R$_4$.

Thus, the nucleophile compound of formula II in which X is NH$_2$ is coupled with an electrophile having the following formula IV:

Formula IV in which Y is I, Br or C$_1$ and R$_6$ is R$_3$ or R$_4$ for obtaining a compound of the following formula V:

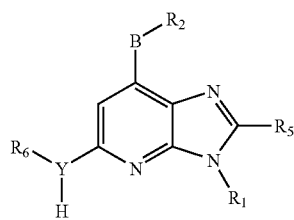

Formula V

The most preferably, Y is I.

Then, when R$_3$ and R$_4$ are different from H, the compound of formula V is coupled with a compound of the following formula VI:

Formula VI in which Y is Br or Cl or I, the most preferably I, and R$_7$ is R$_3$ if in formula V R$_6$ is R$_4$, or R$_7$ is R$_4$ if the compound of formula V R$_6$ is R$_3$.

These coupling steps are carried out, as for the first embodiment of the process of the invention, in basic conditions.

The more preferably, X and Y are I or Br, and the most preferably I, in each occurrence.

The invention will be now described by means of preferred embodiments.

EXAMPLE 1

Preparation of Perharidine B (Compound of Formula Ih)

5,7-Dichloro-3-iso-propylimidazo pyridine 2

A stirred solution of 5,7-Dichloroimidazo[4,5-b]pyridine (5 g, 26.5 mmol.) in DMSO (50 mL) was cooled in an ice bath, and treated with K$_2$CO$_3$ (14.6 g, 106.2 mmol.) and 2-bromopropane (12.47 mL, 132.8 mmol.). The mixture was allowed to warm to 18° C. and stirred overnight. The DMSO was removed in vacuo. A mixture of the residue and water (100 mL) was extracted with AcOEt (3×300 mL). The extractions were combined, washed with brine (300 mL), dried over (Na$_2$SO$_4$) and concentrated. Chromatography of the residue on silica gel with toluene-AcOEt-CH$_2$Cl$_2$ 3:1:1 gave 5,7-Dichloro-3-iso-propylimidazo[4,5-b]pyridine. (Yield: 57%).

$^1$H NMR (400 MHz, CDCl$_3$): δ 1.67 (d, 6H); 5.01 (m, 1H,); 7.95 (s, 1H); 8.39 (s, 1H)

7-Benzylamino-5-chloro-3-iso-propylimidazo[4,5-b]pyridine IIa

A mixture of 2 (1.87 g, 8.1 mmol.), benzylamine (1.4 mL, 13 mmol.) and 1.5 mL of Et$_3$N in 10 mL of DMF was stirred at room temperature overnight under N$_2$ atmosphere. The DMF was removed in vacuo. Water (150 mL) was added and extracted with CH$_2$Cl$_2$ (3×100 mL). The organic phases were dried (Na$_2$SO$_4$) and concentrated. Chromatography of the residue on silica gel with toluene-AcOEt-3:2 gave 3 (82%). 3a could also be prepared upon heating for 1 hour, a mixture of 2, benzylamine and triethylamine in n-butanol at 90° C. After concentration in vacuo, 3a was isolated by column chromatography in 75% yield.

$^1$H NMR (400 MHz, CDCl$_3$): δ 1.5 (d, 6H); 4.49 (d, 2H,); 4.88 (m, 1H); 5.75 (t, 1H); 6.31 (s, 1H); 7.3-7.25 (m, 5H); 7.7 (s, 1H).

Perharidine B: (S)-7-Benzylamino-5-[(2-butyl-1-ol)amino]-3-iso-propylimidazo[4,5-b]pyridine Ib To a suspension of (540 mg, 1.8 mmol) of 7-Benzylamino-5-chloro-3-iso-propylimidazo[4,5-b]pyridine, 3a, in toluene (20 mL) with (S)-(+)-2-Amino-1-butanol, in the presence of palladium acetate (4 mol %), and BINAP (4 mol %) in refluxing toluene (20 mL) using potassium tert-butoxide (282 mg, 2.5 mmol). The reaction mixture was heated under N$_2$ for 5 hours. After cooling water (10 mL) was added and extracted with CH$_2$Cl$_2$ (3×10 mL). The organic layer were dried (Na$_2$SO$_4$) and concentrated. Chromatography of the residue on silica gel with AcOEt-1% MeOH afforded Ib (42%).

$^1$H NMR (400 MHz, CDCl$_3$): δ 0.95 (t, 3H); 1.49 (m, 8H); 3.55 (m, 1H); 3.77 (m, 2H); 4.48 (d, 2H); 4.62 (hept, 1H); 4.85 (brt, 1H); 5.35 (s, 1H); 6.10 (brs, 1H); 7.30 (m, 5H); 7.65 (s, 1H).

EXAMPLE 2

Preparation of Perharidine A (Compound of Formula Ia)

By the first embodiment of the process of the invention, the synthesis of Perharidine A was performed from 3a as described for Perharidine B except that (R)-(−)-2-Amino-1-butanol was used in the last step. Yield: 38%.

EXAMPLE 3

Preparation of Perharidine D (Compound of Formula Id)

The same procedure detailed in example 1 was followed. This product was prepared as described for 3a upon heating in 50 mL n-butanol a mixture of 4-(2-pyridyl)-benzylamine trifluoroacetate (0.15 mol), triethylamine 5 mL and 5,7-Dichloro-3-iso-propylimidazo[4,5-b]pyridine 2 (0.1 mol), 5-Chloro-3-Iso-Propyl-7-[4-(2-pyridyl)-benzylamino]-imidazo[4,5-b]pyridine IIb $^1$H NMR (400 MHz, CDCl$_3$): δ 1.52 (d, 6H, 2 CH$_3$); 4.56 (d, 2H, CH$_2$); 4.94 (hept, 1H, CH, iPr); 5.89 (t, 1H, NH); 6.35 (s, 1H, 6-H); 7.35 m, 1H, pyridyl); 7.45 (d, 2H, phenyl); 7.75 (m, 2H, pyridyl); 7.83 (s, 1H, H-2); 7.95 (d, 2H, phenyl); 8.70 (d, 1H, pyridyl).

Perharidine D: (S)-7-[4-(2-Pyridyl)-benzylaminol]-5-[(2-butyl-1ol)amino]-3-iso-propylimidazo[4,5-b]pyridine Id Yield: 35%.
¹H NMR (400 MHz, CDCl₃): δ 1.03 (t, 3H, CH₃); 1.50 (d, 6H, 2 CH₃); 3.51 (m, 1H, CH—OH); 3.75 (m, 2H, CH—OH+CH—NH); 4.20 (br s, 1H, OH); 4.50 (d, 2H, CH₂—Ar); 5.44 (s, 1H, H-6) 5.85 (t, 1H, NH); 7; 25 (m, 1H, pyridyl); 7.45 (d, 2H, phenyl); 7.65 (s, 1H, H-2); 7.75 (m, 2H, pyridyl); 7.98 (d, 2H, phenyl); 8.70, (d, 1H, pyridyl).

EXAMPLE 4

Preparation of Perharidine C (Compound of Formula Ic)

The synthesis of Perharidine C was performed from IIb as described for Perharidine D except that (R)-(−)-2-Amino-1-butanol was used in the last step. Yield: 47%.

EXAMPLE 5

Preparation of Perharidines from 7-nitroimidazo[4,5-b]pyridine

3-Iso-propyl-7-nitroimidazo[4,5-b]pyridine 4

The alkylation of 7-nitro-imidazo[4,5-b]pyridine 3 was performed in the same conditions than for the synthesis of 2. Yield: 76%.
¹H-NMR (400 MHz, CDCl₃): δ 1.61 (d, 6H, 2 CH₃); 4.99 (hept, 1H, CH, iPr); 7.90 (d, 1H, H-6); 8.36 (s, 1H, H-2); 8.52 (d, 1H, H-5).

3-Iso-Propyl-5,7-dinitro-imidazo[4,5-b]pyridine 5

To a solution of 22.63 g of tetrabutylammonium nitrate in 100 mL CH₂Cl₂ at 0° C., was added 10.33 mL of trifluoroacetic anhydride. After stirring 20 min at 0° C., this solution was added to 3-Isopropyl-7-nitroimidazo[4,5-b]pyridine 3 (10.21, 0.049 mol) in 130 mL CH₂Cl₂ kept at 0° C. after stirring 2 hours at 0° C., the solution is poured into a cold (5° C.) saturated solution of NaHCO₃. The organic layer was washed once with H₂O, dried and concentrated in vacuo. Yield 97%.
¹H NMR (400 MHz, CDCl₃): δ 1.76 (d, 6H, 2CH₃); 5.10 (hept, 1H, CH, iPr); 8.63 (s, 1H, H-2); 8.96 (s, 1H, H-6).

7-Benzylamino-3-Iso-Propyl-5-nitroimidazo[4,5-b]pyridine 6a

To a solution of 5,7-dinitro-3-iso-propylimidazo[4,5-b]pyridine, 5, in DMF was added NEt₃ and benzylamine. After 6 h stirring at 20° C., 15 mL Et₂O was added and the solid which precipitated was filtered and washed with Et₂O.
¹H NMR (400 MHz, CDCl₃): δ 1.65 (d, 6H, 2CH₃); 4.65 (d, 2H, CH₂); 4.92 (hept, 1H, CH, iPr); 6.95 (t, 1H, NH); 7.24 (s, 1H, H-6); 7.42 (m, 5H, phenyl); 7.98 (s, 1H, H-2).

The biarylderivative was prepared by the same process.

3-Iso-Propyl-5-nitro-7-[4-(2-pyridyl)-benzylamino]-imidazo[4,5-b]pyridine 6b

¹H NMR (400 MHz, CDCl₃): δ 1.55 (d, 6H, 2 CH₃); 4.63 (d, 2H, CH₂); 5.01 (hept, 1H, CH, iPr); 6.88 (br s, 1H, NH); 7.22 (m, 1H, pyridyl); 7.49 (d, 2H, phenyl); 7.68 (dd, 1H, pyridyl); 8.01 (d, 2H, phenyl); 8.04 (s, 1H, H-2); 8.66 (d, 1H, pyridyl).

5-Amino-3-Iso-Propyl-7-benzylamino-imidazo[4,5-b]pyridine IIb

To a suspension of 5.5 g of Fe in 30 mL EtOH was added slowly 2 mL 12 N HCl. The mixture was stirred at 75° C. for 1 hour. After cooling at 65° C., 12 mL 25% NH₄Cl solution was added. The mixture was stirred 5 min and 6a (0.02 mol, in 5 mL EtOH) was added. The mixture is heated at 75° C. for 2 hour. After cooling to rt, 5 g celite was added the mixture was filtrated on celite and the remaining solids were washed several times with ethanol. The combined filtrates were concentrated and extracted with a CH₂Cl₂ and 10% Na₂CO₃. Concentration of the organic layer led to crystallisation of the amine IIb. Yield 98%.
¹H NMR (400 MHz, CDCl₃): δ 1.45 (d, 6H, 2CH₃); 4.12 (brs, 2H, NH₂); 4.68 (hept, 1H, CH, iPr); 5.48 (s, 1H, H-6); 5.53 (t, 1H, H-2); 7.15-7.35 (m, 5H, phenyl); 7.55 (s, 1H, H-6).

The biaryl derivative IIc was prepared by the same process.

5-Amino-3-Iso-Propyl-7-[4-(2-pyridyl)-benzylamino]-imidazo[4,5-b]pyridine IIc

Yield: 95%.
¹H NMR (400 MHz, CDCl₃): δ 1.55 (d, 6H, 2 CH₃); 4.55 (d, 2H, CH₂); 4.92 (hept, 1H, CH, iPr); 5.80 (t, 1H, NH); 6.74 (s, 1H, H-6); 7.22 (m, 1H, pyridyl); 7.47 (d, 2H, phenyl); 7.62 (m, 2H, pyridyl); 7.98 (d, 2H, phenyl); 8.70 (m, 1H, pyridyl).

5-Benzylamino-3-Iso-Propyl-7-iodo-imidazo[4,5-b]pyridine IId

Compounds IId have been prepared by the procedure described in the following scheme.

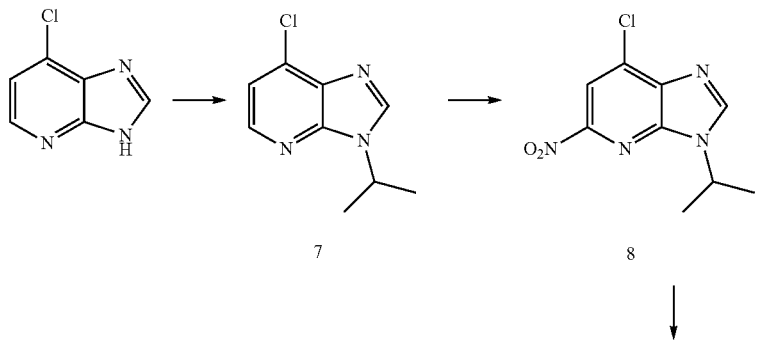

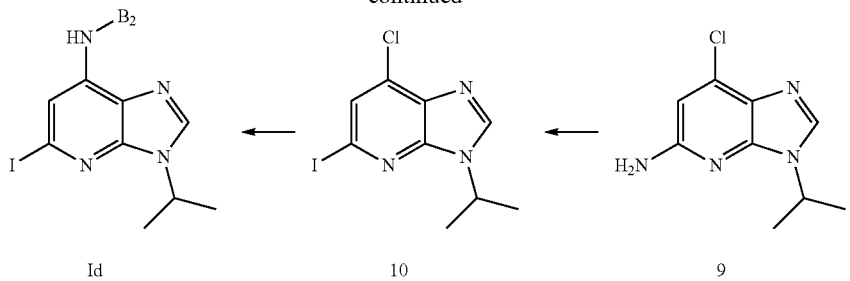

In the first step, the alkylation of 7-chloroimidazo[4,5-b]pyridine as described in the synthesis of compound 2 lead to 7-chloro-3-isopropylimidazo[4,5-b]pyridine 7. Nitration with a mixture of tetrabutyl ammonium nitrate and trifluoroacetic anhydride is then conducted as described in the synthesis of S afforded 7-chloro-3-isopropyl-5-nitroimidazo[4,5-b]pyridine 8. Reduction of the nitro group, following the procedure used in the synthesis of IIb, led to 5-amino-7-chloro-3-isopropyl-imidazo[4,5-b]pyridine 9. In the following step, the amine 9 that was then was converted into 7-chloro-5-iodo-3-isopropylimidazo[4,5-b]pyridine 10 using $CH_2I_2$ and an alkylnitrite (tert-butylnitrite or iso-amylnitrite). Finely, derivative Iid was obtained from 10, as described in the preparation of IIa.

Compounds of general formula V which differ by R1 as defined before could be prepared by the same procedure.

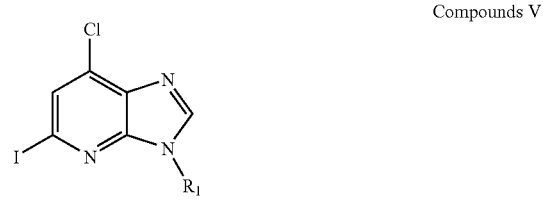

Compounds V 7-chloro-3-isapropylimidazo[4,5-b]pyridine 7

$^1$H NMR (400 MHz, $CDCl_3$): δ 1.65 (d, 6H, 2$CH_3$); 4.98. (hept, 1H, $CH(CH_3)_2$); 7.28 (d, 1H, H-5); 8.18 (s, 1H, H-2). 8.3 (d, 1H, H-6);

7-chloro-3-isopropyl-5-nitroimidazo[4,5-b]pyridine 8

$^1$H NMR (400 MHz, $CDCl_3$): δ 1.75 (d, 6H, 2$CH_3$); 5.12 (hept, 1H, $CH(CH_3)_2$); 8.35 (s, 1H); 8.45 (s, 1H).

5-amino-7-chloro-3-isopropyl-imidazo[4,5-b]pyridine 9

$^1$H NMR (400 MHz, $CDCl_3$): δ 1.60 (d, 6H, 2$CH_3$); 4.50 (bs, 2H, $NH_2$); 4.80 (hept, 1H, $CH(CH_3)_2$); 6.53 (s, 1H, H-8); 7.84 (s, 1H, H-2).

7-chloro-5-iodo-3-isopropylimidazo[4,5-b]pyridine 10

$^1$H NMR (400 MHz, $CDCl_3$): δ 1.65 (d, 6H, 2$CH_3$); 4.95 (hept, 1H, $CH(CH_3)_2$); 7.68 (s, 1H,); 8.07 (s, 1H).

Preparation of IId

To a stirred suspension of 0.1 mol of 5-Amino-3-iso-Propyl-7-benzylamino-imidazo[4,5-b]pyridine IIb in 100 mL $CH_2I_2$ at 60° C. was added slowly 0.2 mol isopentylnitrite. After 1 hour stirring at 60° C., diiodomethane was distilled in vacuo (0.1 mm). The residue was taken up with a mixture of $CH_2Cl_2$ and saturated $NaHCO_3$. The organic layer was separated and washed with $H_2O$, dried and concentrated to afford IId.

Yield: 95%.

$^1$H NMR (400 MHz, $CDCl_3$): δ 1.51 (d, 6H, 2 $CH_3$); 4.40 (d, 2H, $CH_2$); 4.82 (hept, 1H, CH, iPr); 5.56 (t, 1H, NH); 6.64 (s, 1H, H-6); 7.28 (m, 5H, phenyl); 7.75 (s, 1H, H-2).

The biaryl derivative IIe was prepared by the same process.

3-Iso-Propyl-7-iodo-5-[4-(2-pyridyl)-benzylamino]-imidazo[4,5-b]pyridine IIe

Yield: 95%.

$^1$H NMR (400 MHz, $CDCl_3$): δ 1.55 (d, 6H, 2 $CH_3$); 4.55 (d, 2H, $CH_2$); 4.92 (hept, 1H, CH, iPr); 5.80 (t, 1H, NH); 6.74 (s, 1H, H-6); 7.22 (m, 1H, pyridyl); 7.47 (d, 2H, phenyl); 7.62 (m, 2H, pyridyl); 7.98 (d, 2H, phenyl); 8.70 (m, 1H, pyridyl).

3-Iso-Propyl-5-(4-N-acetylcyclohexylamino)-7-(benzylamino)-imidazo[4,5-b]pyridine Ih To a mixture of $K_3PO_4$ (900 mg, 0.022 mol), CuI (50 mg, 0.25 mmol), was added 4 mL 1-butanol, 0.5 mL ethyleneglycol, (0.010 mol) 5-Benzylamino-3-Iso-Propyl-7-iodo-imidazo[4,5-b]pyridine IId and trans-4-N-acetylaminocyclohexylamine (0.010 mol). The flask was flushed with nitrogen, closed and heated for 18 h at 90° C. After cooling to rt, The residue was taken up with a mixture of $CH_2Cl_2$ and $H_2O$. The organic layer was dried and concentrated. Column chromatography gave 3-Iso-Propyl-5-N-acetyl cyclohexylamino-7-[4-(2-pyridyl)-benzylamino]-imidazo[4,5-b]pyridine, Yield 94%.

$^1$H NMR (400 MHz, $CDCl_3$): δ 1.35 (m, 4H, cyclohexyl); 1.56 (d, 6H, 2$CH_3$); 1.98 (s, 3H, $CH_3CO$); 2.20 (m, 4H, cyclohexyl); 3.45 (m, 1H, cyclohexyl); 3.75 (m, 1H, cyclohexyl); 4.5 (d, 2H, $CH_2$); 4.69 (hept, 1H, iPr); 5.32 (d, 1H, NH); 5.35 (s, 1H, H-6); 5.65 (br s, NH); 7.35 (m, 5H, phenyl); 7.58 (s, 1H, H-2).

Similarly, perharidines A, B, C and D were obtained from the iododerivatives IId or IIe in 79 to 95% yield.

EXAMPLE 6

3-Iso-Propyl-5-(1,3-dihydroxypropylamino)-7-[4-(2-pyridyl)-benzylamino]-imidazo[4,5-b]pyridine. Ii, Perharidine E

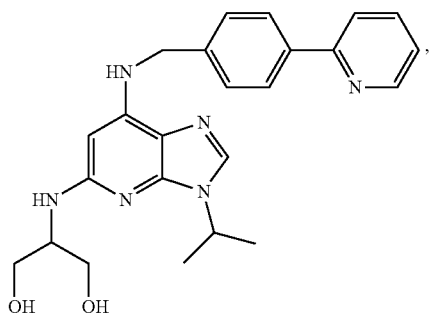

Compound Ii

Perharidine E $^1$H-NMR: 1.45 (d, 6H); 3.55-3.80 (m, 51-1); 4.38 (d, 2H); 4.55 (hept, 1H); 4.90 (bs, 1H); 5.35 (s, 1H); 5.75 (t, 1H); 7.15 (m, 1H); 7.30 (d, 1H) 7.5 (s, 1H); 7.65 (m, 2H); 7.85 (d, 2H); 8.6 (d, 1H).

In connection to the following examples 7 to 14, some obtained compounds have been tested biologically. The materials and methods as exposed hereinafter for examples 1-6 have been used.

EXAMPLE 7

(R,R)-2-[[3-isopropyl-7-[[4-(2-pyridyl)phenyl]methylamino]imidazo[4,5-b]pyridin-5-yl]amino]butane-1,3-diol. Ij

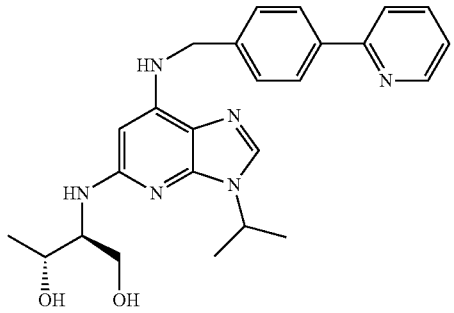

Compound Ij

By using the procedure described in the preparation of Ih: amino-alcohol, $K_3PO_4$, CuI, $HOCH_2CH_2OH$ in n-butanol, the compound Ij was prepared.

Yield 78%. $^1$H-NMR 1.20 (d, 3H, $CH_3CH$); 1.52 (d, 6H, 2 $CH_3$, iPr); 3.73 (br s, 1H,); 3.80 (m, 1H); 3.85 (m, 1H); 4.05 (t, 1H); 4.50 (d, 2H, $CH_2N$); 4.65 (hept, 1H, CH iPr); 4.98 (d, 1H); 5.48 (s, 1H, 6-H); 5.72 (t, 1H, $\underline{NH}CH_2$); 7.25 (t, 1H, pyridine); 7.40 (d, 2H, phenyl); 7.58 (s, 1H, 2-H); 7.70 (m, 2H, pyridine); 7.95 (m, 2H, phenyl); 8.70 (d, 1H, pyridine).

Inhibition of kinases were as follows: CDK1/cyclin B: $IC_{50}$=0.15 µM; CDK5/p25=0.18 µM/cyclin; CDK9/cyclin T: $IC_{50}$=0.14 µM; CK1: $IC_{50}$=0.53 µM; GSK3beta: $IC_{50}$=13 µM. Inhibition of the tumor cell-line SHSY-5Y was determined: $IC_{50}$=0.15 µM.

EXAMPLE 8

(2S)-3-[[3-isopropyl-7-[[4-(2-pyridyl)phenyl]methylamino]imidazo[4,5-b]pyridin-5-yl]amino]propane-1,2-diol. Ik

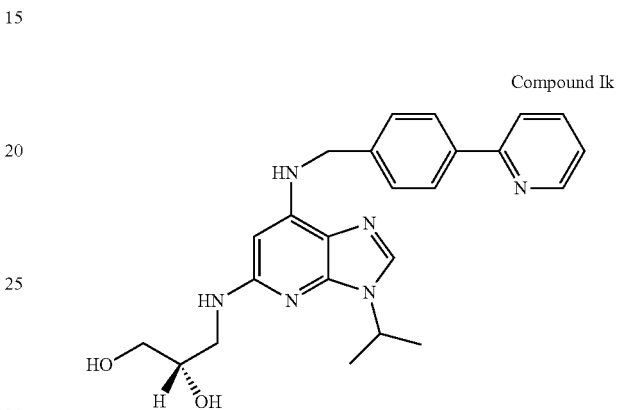

Compound Ik

By using the procedure described in the preparation of Ih: amino-alcohol, $K_3PO_4$, CuI, $HOCH_2CH_2OH$ in n-butanol, the compound Ik was prepared.

Yield 65%. $^1$H-NMR ($CDCl_3$): 1.55 (d, 6H); 3.62 (m, 4H, $CH_2O$ and $CH_2N$); 3.85 (m, 1H, CHO); 4.62 (hept, 1H, 4.82 (br s, 1H); 5.40 (d, 2H, $CH_2Aro$); 5.48 (s, 1H, 6-H); 5.70 (t, 1H, NH) 7.22 (t, 1H, pyridine); 7.43 (d, 2H, phenyl); 7.60 (s, 1H, 2-H); 7.72 (m, 2H, pyridine); 7.93 (m, 2H, phenyl); 8.68 (d, 1H, pyridine).

Inhibition of kinases were as follows: CDK1/cyclin B: $IC_{50}$=0.20 µM; CDK2/cyclin A: $IC_{50}$=0.12; CDK5/p25=0.17 µM/cyclin; CK1: $IC_{50}$=0.38 µM; GSK3beta: $IC_{50}$>10 µM.

Inhibition of the tumor cell-line SHSY-5Y was determined. $IC_{50}$=0.18 µM

EXAMPLE 9

(2S)-2-[[3-isopropyl-7-[(4-phenylphenyl)methylamino]imidazo[4,5-b]pyridin-5-yl]amino]butan-1-ol. Il

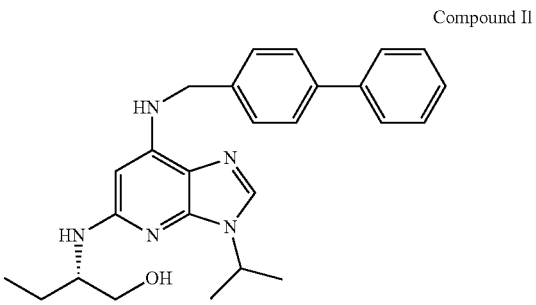 [SMILES: CC[C@@H](CO)Nc1cc(NCc2ccc(-c3ccccc3)cc2)c2ncn(C(C)C)c2n1]

Compound Il

The iododerivative IIe was prepared from the corresponding amine as described in the synthesis of IId using diiodomethane and isopentyl or tert-butylnitrite.

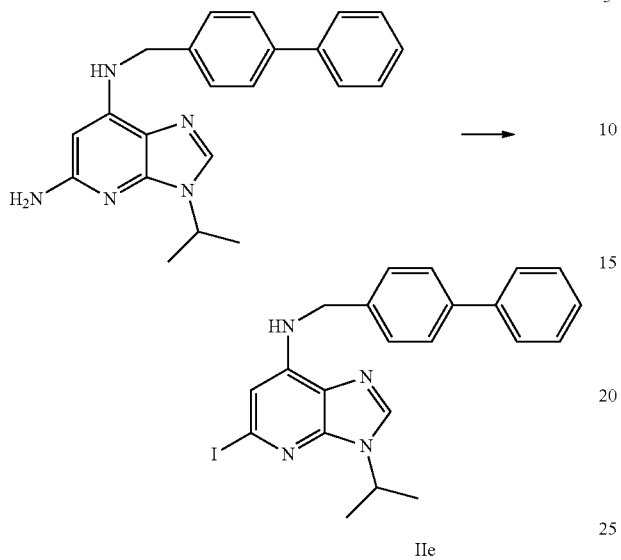

IIe 5-iodo-3-isopropyl-N-[(4-phenylphenyl)methyl]imidazo[4,5-b]pyridin-7-amine, IIe.

Yield 65%. $^1$H NMR (CDCl$_3$): 1.56 (d, 6H, J=6.82 Hz, CH(CH$_3$)$_2$), 4.54 (d, 2H, J=5.55 Hz, CH$_2$—NH), 4.8 (hept, 1H, J=6.82 Hz, CH(CH$_3$)$_2$), 5.72 (bs, 1H, NHCH$_2$), 6.76 (s, 1H, 6-H), 7.35 (m, 1H,), 7.43 (m, 4H), 7.59 (d, J=6.82 Hz, 4H), 7.75 (s, 1H, 2-H)

IIe was reacted in conditions used in the synthesis of Ih: amino-alcohol, K$_3$PO$_4$, CuI, HOCH$_2$CH$_2$OH in n-butanol, the compound Il was prepared.

$^1$H-NMR (CDCl$_3$): 1.55 (d, 6H) 4.28 (brs, 1H); 4.50 (d, 2H, CH$_2$—Ar); 4.68 (hept, 1H, CH(CH$_3$)$_2$, 5.48 (s, 1H, 6-H); 5.71 (t, 1H, NH); 7.35 (m, 1H, Ar); 7.40 (m, 4H, Ar); 7.60 (m, 5H, Ar+2-H).

This compound was tested against kinases. Inhibition of CDK5/p25: IC$_{50}$=0.60 CK1 IC$_{50}$=2 µM; GSK3beta: IC$_{50}$>10 µM; DYRK1A: IC$_{50}$=4.5 µM.

EXAMPLE 10

(R) 2-[[3-isopropyl-7-[(4-phenylphenyl)methylamino]imidazo[4,5-b]pyridin-5-yl]amino]butan-1-ol. Im

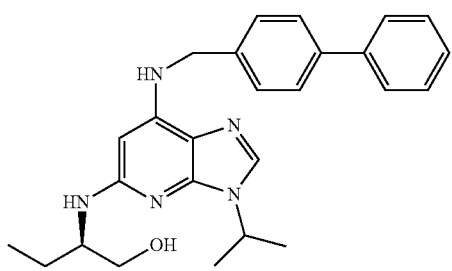

Im

Im was obtained in the same conditions than for the S-enantiomer. That is to say heating (R)-2-aminobutan-1-ol, K$_3$PO$_4$, CuI, HOCH$_2$CH$_2$OH in n-butanol, the compound Im was prepared.

Yield 83%. $^1$H-NMR (CDCl$_3$): 1.55 (d, 6H) 4.28 (brs, 1H); 4.50 (d, 2H, CH$_2$—Ar); 4.70 (hept, 1H, CH(CH$_3$)$_2$; 5,48 (s, 1H, 6-H); 5.65 (t, 1H, NH); 7.35 (m, 1H, Ar); 7.40 (m, 4H, Ar); 7.60-7.80 (m, 5H, Ar+2-H).

This compound was tested against kinases. Inhibition of CDK5/p25: IC$_{50}$=0.81 µM; CK1 IC$_{50}$=1.2 µM.

EXAMPLE 11

(R)-5-(2-aminobutoxy)-3-isopropyl-N-[(4-phenylphenyl)methyl]imidazo[4,5-b]pyridine-7-amine. In

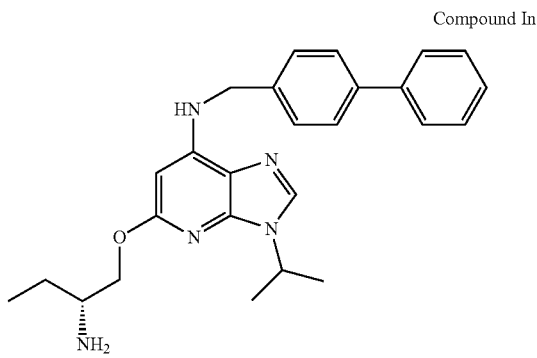 [SMILES: CC[C@@H](N)COc1cc(NCc2ccc(-c3ccccc3)cc2)c2ncn(C(C)C)c2n1]

Compound In

A mixture of compound IIe (0.5 mg); CuI (0.05 g), K$_3$PO$_4$ (1 g) were introduced in a screw-cap tube. The reaction vessel was fitted with a rubber septum. The vessel was evacuated and back-filled with nitrogen using syringe needles. This last sequence was repeated twice. N-Butanol 1.5 mL, (R)-aminobutanol (1 mL) and ethyleneglycol (0.267 mL), were introduced in this order to the stirred solids. The reaction tube was sealed, and stirred in an oil bath for 48 h at 110° C. After cooling to rt, a 5% EDTA solution (1 mL) was added and the mixture was extracted with CH$_2$Cl$_2$ (3×10 mL). Compounds Im and In were separated by column chromatography using CH$_2$Cl$_2$-EtOH-NEt$_3$ as eluent (90:10:0.5 followed by 85:15:0.5). Compound Im was eluted first (yield 43%) followed by In.

In: Yield 32%. (CDCl$_3$): 0.95 (t, 3H, CH$_3$—CH$_2$); 1.45 (q, CH$_2$—CH$_3$); 1.55 (d, 6H, CH(CH$_3$)$_2$); 1.78 (br s, 2H, NH$_2$): 3.08 (m, 1H, CH—NH$_2$); 4.05 (t, 1H, HCO); 4.32 (dd, 1H, HCO); 4.52 (d, 2H, CH$_2$—Ar); 4.75 (hept, 1H, CH(CH$_3$)$_2$; 5.65 (t, 1H, NH); 5.80 (s, 1H, 6-H); 7.35 (m, 1H, Ar); 7.40 (m, 4H, Ar); 7.60 (m, 4H, Ar); 7.70 (s, 1H, 2-H).

Inhibition of kinases were as follows: CDK5/p25: IC$_{50}$=0.55 µM/cyclin; CK1: IC$_{50}$=0.12 µM; GSK3beta: IC$_{50}$=7 µM; DYR1A 4.0 µM.

EXAMPLE 12

(R)-5-(2-aminobutoxy)-3-isopropyl-N-[(4-phenylphenyl)methyl]imidazo[4,5-b]pyridin-7-amine hydrochloride. Io

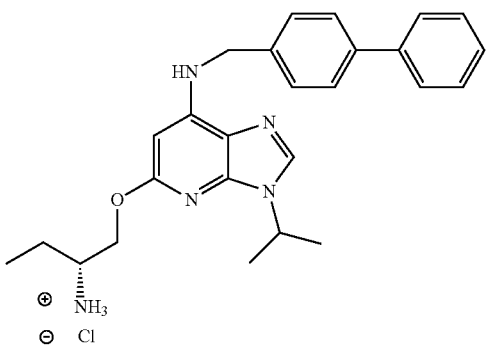

Io

The hydrochloride was prepared upon adding an ethereal solution of HCl to a solution of In in diethyl ether.

Yield: 97%. $^1$H-NMR (DMSOd6): 0.98 (t, 3H, CH$_3$CH$_2$); 1.60 (d, 6H, 2CH$_3$); 3.40 (m, 1H CHN); 4.30 and 4.50 (m, 1H, CHO); 4.60 (br s, 2H, CH$_2$); 7.30 (t, 1H, aro); 7.40-7.65 (m, 8H); 8.20 (br s, 2H); 8.50 (s, 1H); 9.45 (br s, 1H).

EXAMPLE 13

(S)-5-(2-aminobutoxy)-3-isopropyl-N-[(4-phenylphenyl)methyl]imidazo[4,5-b]pyridin-7-amine. Ip Compound Ip

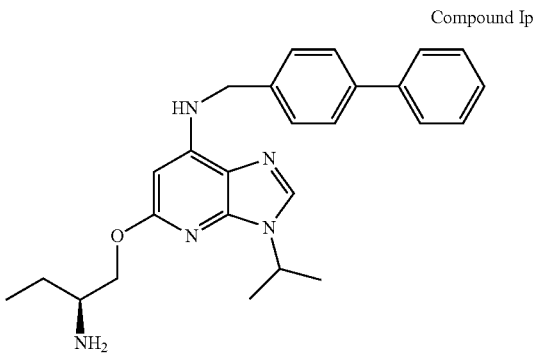 [SMILES: CC[C@H](N)COc1cc(NCc2ccc(-c3ccccc3)cc2)c2ncn(C(C)C)c2n1]

Similarly as in the synthesis of In, when IIe at 120° C., with S-2-aminobutan-1-ol, K$_3$PO$_4$, CuI, HOCH$_2$CH$_2$OH in butanol, the O-alkyl derivative Ip, was obtained in moderate yield Yield 25%. (CDCl$_3$): 0.95 (t, 3H, CH$_3$—CH$_2$); 1.45 (q, CH$_2$—CH$_3$); 1.55 (d, 6H, CH(CH$_3$)$_2$); 1.80 (br s, 2H, NH$_2$): 3.0 (m, 1H, CH—NH$_2$); 4.05 (t, 1H, HCO); 4.3 (dd, 1H, HCO); 4.50 (d, 2H, CH$_2$—Ar); 4.75 (hept, 1H, CH(CH$_3$)$_2$; 5.65 (t, 1H, NH); 5.80 (s, 1H, 6-H); 7.35 (m, 1H, Ar); 7.40 (m, 4H, Ar); 7.60 (m, 4H, Ar); 7.70 (s, 1H, 2-H).

Inhibition of kinases were as follows: CDK5/p25: IC$_{50}$=0.4904/cyclin; CK1: IC$_{50}$=0.22 µM; GSK3beta: IC$_{50}$=7 µM; DYR1A: 3.3 µM.

EXAMPLE 14

(S)-5-(2-aminobutoxy)-3-isopropyl-N-[(4-phenylphenyl)methyl]imidazo[4,5-b]pyridin-7-amine hydrochloride. Iq

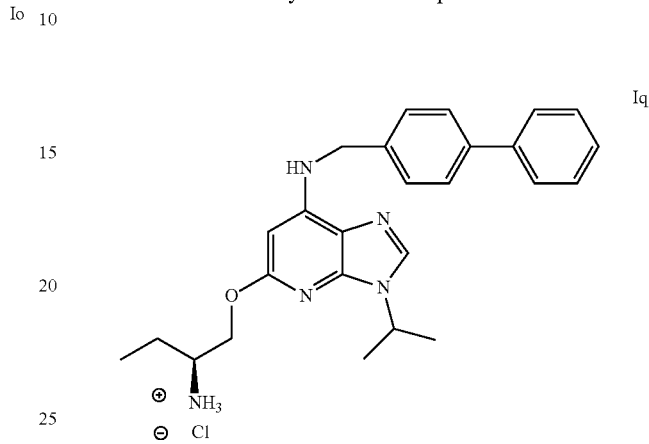

Iq

The hydrochloride was prepared upon adding an ethereal solution of HCl to a solution of In in diethyl ether.

Yield: 90%. $^1$H-NMR (DMSO-d6): 1.0 (t, 3H, CH$_3$CH$_2$); 1.60 (d, 6H, 2CH$_3$); 3.40 (m, 1H CHN); 4.30 and 4.50 (m, 1H, CHO); 4.60 (br s, 2H, CH$_2$); 7.30 (t, 1H, are); 7.40-7.65 (m, 8H); 8.20 (br s, 2H); 8.50 (s, 1H); 9.50 br s, 1H).

The compounds obtained in examples 1-6 have been tested to determine their effects on different kinases and cell lines.

The following materials and methods have been used.

Buffers

Buffer A: 10 mM MgCl$_2$, 1 mM EGTA, 1 mM DTT, 25 mM Tris-HCl pH 7.5, 50 µg heparin/ml.

Buffer C: 60 mM β-glycerophosphate, 15 mM p-nitrophenylphosphate, 25 mM MOPS (pH 7.2), 5 mM EGTA, 15 mM MgCl$_2$, 1 mM DTT, 1 mM sodium vanadate, 1 mM phenylphosphate.

Kinase Preparations and Assays

Kinase activities were assayed in Buffer A or C, at 30° C., at a final ATP concentration of 15 µM. Blank values were subtracted and activities expressed in % of the maximal activity, i.e. in the absence of inhibitors. Controls were performed with appropriate dilutions of dimethylsulfoxide.

CDK1/cyclin B (M phase starfish oocytes, native) and CDK5/p25 (human, recombinant) were prepared as previously described (Leclerc S. et al., J Biol Chem 2001; 276: 251-60.). Kinase activity was assayed in buffer C, with 1 mg histone H1/ml, in the presence of 15 µM [γ-$^{33}$P] ATP (3,000 Ci/mmol; 10 mCi/ml) in a final volume of 30 µl. After 30 min. incubation at 30° C., 25 µl aliquots of supernatant were spotted onto 2.5×3 cm pieces of Whatman P81 phosphocellulose paper, and, 20 sec. later, the filters were washed five times (for at least 5 min. each time) in a solution of 10 ml phosphoric acid/liter of water. The wet filters were counted in the presence of 1 ml ACS (Amersham) scintillation fluid.

CDK2/cyclin A (human, recombinant, expressed in insect cells) was assayed as described for CDK1/cyclin B.

CDK9/cyclin T (human, recombinant, expressed in insect cells) was assayed as described for CDK1/cyclin B, but using a pRB fragment (amino acids. 773-928) (3.5 µg/assay) as a substrate.

GSK-3α/β (porcine brain, native, affinity purified) was assayed, as described for CDK1 but in Buffer A and using a GSK-3 specific substrate (GS-1: YRRAAVPPSPSLSRHSSPHQSpEDEEE (SEQ ID NO:1) (Sp stands for phosphorylated serine) (Bach S. et al. J Biol Chem 2005; 280:31208-19).

CK1δ/ε (porcine brain, native, affinity purified) was assayed as described for CDK1 but using the CK1-specific peptide substrate RRKHAAIGSpAYSITA (SEQ ID NO:2) (Reinhardt J. et al. Protein Expr & Purif 2007; 54:101-9).

Cell Biology
Antibodies & Chemicals

AcDEVDafc and Q-VD-OPh were purchased from MPbiomedicals (Vannes, France). Cell Titer 96® containing the MTS reagent and CytoTox 96® kits were purchased from Promega (Madison, Wis., USA). The protease inhibitor cocktail was from Roche (Penzberg, Germany). Unless otherwise stated, the non-listed reagents were from Sigma.

Monoclonal antibody against actin was obtained from Calbiochem (Madison, Wis., USA). Monoclonal antibodies against retinoblastoma protein (Rb) were purchased from BD Biosciences (San Diego, Calif., USA). Polyclonal antibody against phospho-Ser249/Thr252-Rb was provided by Biosource (Camarillo, Calif., USA). Polyclonal antibody against phospho-Thr320-protein phosphatase 1α, (PP1α) and monoclonal antibody against caspase-9 were from Cell Signalling (Danvers, Mass., USA). Polyclonal antibodies against RNA polymerase II and phospho-Ser2-RNA polymerase II were supplied by Covance Research Products (Berkeley, Calif., USA). Polyclonal antibody against Mcl-1 was obtained from Santa Cruz Biotechnology (Santa Cruz, Calif., USA).

Cell Lines and Culture Conditions

SH-SY5Y human neuroblastoma cells were grown in DMEM medium (Invitrogen, Cergy Pontoise, France). The HEK 293 human embryonic kidney cell line was grown in MEM medium from Invitrogen. Human foreskin primary fibroblasts (kindly provided by Dr. Gilles Ponzio) were grown in DMEM supplemented with 2 mM L-glutamine and 20 mM HEPES. All the media were supplemented with antibiotics (penicillin-streptomycin) from Lonza and 10% volume of FCS from Invitrogen. Cells were cultured at 37° C. with 5% $CO_2$. Drug treatments were performed on exponentially growing cultures at the indicated time and concentrations. Control experiments were carried out using appropriate dilutions of DMSO. MDCK cell-lines were used to test compounds PKD.

Cell Death and Cell Viability Assessments

Cell viability was determined by measuring the reduction of 3-(4,5-dimethylthiazol-2-yl)-5-(3-carboxymethoxyphenyl)-2-(4-sulfophenyl)-2H-tetrazolium (MTS). Cell death was determined by measuring the level of lactate dehydrogenase activity (LDH) released upon cell lysis. Both procedures have been previously described in detail (Ribas J. et al. Oncogene 2006; 25:6304-18).

Caspase Assay

Caspase activity was measured by determining the fluorescence released from the AcDEVDafc synthetic substrate after its direct addition to the culture medium, detergent lysis, and incubation at 37°. This method is devised for a 96 multiwell plate format. It allows kinetic determinations of caspase activation and the characterization of multiple drugs simultaneously (Ribas J. et al. Oncogene 2006, 25:6304-18), Electrophoresis and Western Blotting Cells were resuspended and lysed for 30 minutes at 4° C. in Homogenization Buffer [60 mM β-glycerophosphate, 15 mM p-nitrophenyl phosphate, 25 mM MOPS (pH 7.2), 15 mM EGTA, 15 mM $MgCl_2$, 1 mM dithiothreitol, 1 mM sodium vanadate, 1 mM NaF, 1 mM phenylphosphate, 0.1% Nonidet P-40 and protease inhibitor cocktail] and sonicated. After centrifugation (14000 rpm for 15 minutes at 4° C.), the protein concentration was determined in the supernatants by the Bradford protein assay (Bio-Rad).

Whole cell extracts were prepared in buffer containing 100 mM Tris/HCl (pH, 6.8), 1 mM EDTA, 2% SDS and protease inhibitor cocktail. Following heat denaturation for 5 minutes, proteins were separated on 10% or 7% NuPAGE pre-cast Bis-Tris or Tris-Acetate polyacrylamide mini gels (Invitrogen) with MOPS SDS (all but cytochrome C, RNA polymerase II and phospho-Ser2—RNA polymerase II Western blots), MES SDS (cytochrome C), or Tris-Acetate SDS (RNA polymerase II and phospho-Ser2—RNA polymerase II) running buffer depending on protein size. Proteins were transferred to 0.45 μm nitrocellulose filters (Schleicher and Schuell). These were blocked with 5% low fat milk in Tris-Buffered Saline—Tween-20, incubated for 1 h with antibodies (anti-actin: 1:2000) or overnight at 4° C. (cytochome C: 1:500), Rb (1:500), phosphor-Rb (1:500), phospho-Thr320-PP1α (1:1000), RNA polymerase II (1:500), phosphor-Ser2-RNA polymerase II (1:500), Mcl-1 (1:500), caspase-9 (1:1000) and analyzed by Enhanced Chemiluminescence (ECL, Amersham).

Results of the Biological Tests.
Effects of the Compounds of the Invention
Effects on Purified Kinases Perharidine A and B (S and R isomers) and their precursors were tested on various isolated, purified disease relevant protein kinases. (R)-Roscovitine was tested in parallel and used as a reference compound. Results are provided as IC50 values expressed in μM in the following Tables 4 and 5.

TABLE 4

Effects of perharidine and its precursors on kinases and cell survival in two cell lines.

| Tested compounds | Name | CDK1 | CDK5 | CDK7 | GSK3 | CK1 | SH-SY5Y | HEK293 |
|---|---|---|---|---|---|---|---|---|
| (structure) | Formula Ie | 1.0 | 0.8 | — | >10.0 | 1.0 | 74.0 | 46.0 |

TABLE 4-continued

Effects of perharidine and its precursors on kinases and cell survival in two cell lines.

| Tested compounds | Name | CDK1 | CDK5 | CDK7 | GSK3 | CK1 | SH-SY5Y | HEK293 |
|---|---|---|---|---|---|---|---|---|
| (structure) | Formula If | 4.0 | 3.8 | — | >10.0 | 8.0 | >100.00 | >100.00 |
| (structure) | Formula Ig | 0.53 | 0.63 | — | >10.0 | 3.0 | >100.00 | >100.00 |
| (structure) | (R)-perharidine A Formula Ia | 0.35 | 0.20 | 0.9 | >30.0 | 4.0 | 16.2 | 35.6 |
| (structure) | (R)-Roscovitine | 0.35 | 0.20 | 0.8 | >10.0 | 2.3 | 19.0 / 18.2 | 60.6 / 39.2 |

The results presented in table 4 show the different intermediates that were synthesized to allow the synthesis of perharidines. Example 1b is the closest homolog to Roscovitine and their biological effects are compared. This shows that compound Ib displays very similar effects on isolated kinases as Roscovitine but improved efficacy on cell proliferation.

As to Perharidine E, Compound Ii, it presents an $IC_{50}$ on CDK5 of 0.34 μM and on CK1 of 0.28 μM.

The compounds were tested at various concentrations in the kinase assays, as described in the Methods section. $IC_{50}$ values were calculated from the dose-response curves shown and are reported in μM in the following table 5.

TABLE 5

Effects of Roscovitine and its perharidine analogs on the activity of 10 protein kinases targets.

| Kinase | (R)-roscovitine | (R)-perharidine A (compound Ia) | (S)-perharidine B (compound Ib) | (R) perharidine C (compound Ic) | (S) perharidine D (compound Id) |
|---|---|---|---|---|---|
| CDK1/cyclin B | 0.33 | 0.43 | 0.73 | 0.46 | 0.27 |
| CDK2/cyclin A | 0.21 | 0.30 | 0.42 | 0.36 | 0.15 |
| CDK2/cyclin E | 0.17 | 0.18 | 0.31 | 0.25 | 0.10 |
| CDK5/p25 | 0.28 | 0.40 | 0.50 | 0.60 | 0.20 |
| CDK7/cyclin H | 0.80 | 0.90 | — | — | — |
| CDK9/cyclin T | 0.23 | 0.48 | 1.30 | 0.53 | 0.12 |
| CK1 | 4.00 | 11.0 | 4.80 | 1.10 | 1.90 |
| DYRK1A | 3.00 | 2.80 | 22.00 | 11.00 | 2.80 |
| Erk2 | 11.00 | 7.00 | 9.00 | 22.00 | 9.00 |
| GSK-3α/β | 60.00 | >100.00 | >30.00 | 11.00 | 24.5 |

Table 5 shows that, like (R)-perharidine (compound of formula Ia), its (S)-isomer (compound of formula Ib), as well as the compounds of formula Ic and Id show efficacies on CDKs which are similar to those of (R)-Roscovitine. However, CDK9 and DYRK1A appear to be somewhat less sensitive to these deazapurines than to (R)-Roscovitine.

Effects of Perharidines on Cell Survival

Perharidine A and B (R and S isomers) and their precursors, as well as the compounds of formula Ic and Id, were tested on various cell lines (assay of survival level with the MTS assay). (R)-Roscovitine was tested in parallel and used as a reference compound. Results are provided as $IC_{50}$ values expressed in µM in FIGS. 3 and 5 and Tables 4 as well as in the following Table 6:

TABLE 6

Effects of Roscovitine and perharidine on cell survival in 5 cell lines.

| Cells | (R)-Roscovitine | (R)-Perharidine A | (S)-Perharidine B | Compound of formula Ic | Compound of formula Id |
|---|---|---|---|---|---|
| SH-SY5Y | 17.0 | 14.3 | 28.0 | 1.46 | 0.66 |
| HEK293 | 21.0 | 27.4 | 45.0 | — | — |
| LS 174T | 26.0 | 21.5 | 37.5 | — | — |
| LS 174T (Oncodesign) | 9.25 | — | — | 0.29 | 0.099 |
| HCT116 | 20.8 | — | — | — | — |
| HCT116 (Oncodesign) | 6.97 | — | — | 0.60 | 0.30 |
| HCT116 (Spheroids) | 7 + 4 | 10 + 1.5 | — | 0.35 + 0.05 | |
| Chronic Lymphocytic Leukemia | 8.96 | 7.05 | 15.27 | 0.31 | 0.13 |

The effects of these compounds were also evaluated on:
cell survival. The results are shown in FIGS. 3 and 5,
caspase activation. The results are shown in FIGS. 4 and 6,
retinoblastoma protein phosphorylation on CDK2/CDK4 sites.

The results are shown in FIGS. 6 and 7.

It can be concluded from FIG. 6 that compound Ic inhibits CDK2/4 in cells at lower concentrations than (R)-Roscovitine, while the compound of Formula Ia and the compound of Formula Ib have an effect similar to the one of (R)-Roscovitine and it can be concluded from FIG. 8 that with (R)-Roscovitine and the compounds of Formula Ia, Ib and Ic, the total Rb is essentially constant.

RNA polymerase II Ser2 phosphorylation), a CDK9/cyclin T phosphorylation site.

The results are shown in FIGS. 9 and 10.

It can be concluded from FIG. 9 that the compound of compound Ic inhibits CDK9 in cells at lower concentration than (R)-Roscovitine, while the compounds of Formula Ia and the compound of Formula Ib have an efficiency similar to the one of (R)-Roscovitine and it can be concluded from FIG. 10 that the total RNA pol II remains essentially constant as well with (R)-Roscovitine as with the compounds of Formula Ia, of Formula Ib, and of Formula Ic, protein phosphatases 1-α phosphorylation on Thr320, a CDK1/cyclin phosphorylation site.

The results are shown in FIG. 11.

It can be concluded from FIG. 11 that the compound of Formula Ic inhibits CDK1/cyclin 13 in cells at lower concentration than (R)-Roscovitine while the compounds of Formula Ia and of Formula Ib have an efficacy similar to the one of (R)-Roscovitine, down-regulation of survival factor Mel-1.

The results are shown in FIG. 12.

It can be concluded from FIG. 12 that the compound of Formula Ic down-regulates the survival factor Mcl-1 in cells at lower concentration than (R)-Roscovitine, while compounds of Formula Ia and of Formula Ib have a potency similar to the one of (R)-Roscovitine, p53 total protein expression.

The results are shown in FIG. 13.

It can be concluded from FIG. 13 that compounds of Formula Ic triggers p53 total protein expression in cells at lower concentration than (R)-Roscovitine, while the compounds of Formula Ia and of Formula Ib have an efficacy similar to the one of (R)-Roscovitine, p27 total protein down-regulation.

The results are shown in FIG. 14.

It can be concluded from FIG. 14 that the compounds of Formula Ic down-regulates p27 total protein in cells at lower concentration than (R)-Roscovitine, while the compounds of Formula Ia and of Formula Ib have an efficacy similar to the one of (R)-Roscovitine, PARP cleavage.

The results are shown in FIG. 15.

It can be concluded from FIG. 15 that the compounds of Formula Ic triggers PARP cleavage in cells at lower concentration than (R)-Roscovitine, while the compounds of Formula Ia and of Formula Ib have a potency similar to the one of (R)-Roscovitine.

Actin total protein levels were used as a loading control with all compounds. The results are shown in FIG. 16, demonstrating equal loading in the gels.

To summarize, these results show that:

[1] the compounds of Formula Ia and of Formula Ib exhibit anti-proliferative activities similar to those displayed by (R)-Roscovitine. The (5) isomer (compound of formula Ib) is somewhat less efficient, as reported for the (S)-isomer of Roscovitine.

[2] in contrast, and quite surprisingly, compound of formula Ic and Id display greatly enhanced anti-proliferative activities as compared to (R)-Roscovitine (20-100 fold), despite the fact that they have rather similar effects on kinases. Unexpectedly too, in contrast to (R)-Roscovitine, the (S) isomer is more active than the (R) isomer (Table 6).

[3] these effects and order of potency are confirmed when molecular actors involved in markers of CDK inhibition (CDK2/CDK4: retinoblastoma protein phosphorylation; CDK1: protein phosphatase I a Thr320 phosphorylation; CDK9: RNA polymerase II Ser2 phosphorylation, p27 down-regulation) and apoptotic cell death are analyzed (p53 expression, down-regulation of survival factor Mcl-1, caspase activation, PARP cleavage) (FIGS. 4-9).

These compounds are thus greatly advantageous over Roscovitine in their effects on induction of cell death and cell proliferation arrest, despite apparently similar effects on their CDK targets. These results appear to correlate with reduced interactions with secondary targets such as pyridoxal kinase (FIG. 1).

Effects of roscovitine and analogues on the survival of B2-CLL lymphocytes and on kinase activity of a representative CDK. (R)-roscovitine and some of the perharidines were tested at various concentrations on isolated B2-CLL lymphocytes obtained from patients. Cell viability was determined by measuring the reduction of 3-(4,5-dimethylthiazol-2-yl)-5-(3-carboxymethoxyphenyl)-2-(4-sulfophenyl)-2/H-tetrazolium (MTS). Cell death was determined by measuring the level of lactate dehydrogenase activity (LDH) released upon cell lysis. Both procedures have been previously described in detail in Ribas J, Boix J. Cell differentiation, caspase inhibition, a nd macromolecular synthesis blockage, but not BCL-2 or BCL-XL proteins, protect SH-SYSY cells from apoptosis triggered by two CDK inhibitory drugs. Exp. Cell Res. 2004; 295, 9-24.

The same compounds were tested on LLC B-cells. $IC_{50}$ values, calculated from the dose-response curves, are reported in µM in the following table.

| Compounds | Cell death induction |
|---|---|
| Roscovitine | 8.96 |
| (R)-perharidine A | 7.05 |
| (S)-perharidine B | 15.27 |
| (R)-perharidine C | 0.31/0.28 |
| (S)-perharidine D | 0.13 |

In order to evaluate the interest of perharidines in PKD, compounds of the invention were also tested on MDCK cells. Perharidines D and E were found 50 to 70 times more potent than roscovitine.

Furthermore, compound Ii was also tested. It appears to be a potent kinase inhibitor with, in particular, $IC_{50}$ on CDK5 and CK1 of 0.35 and 0.28 µM.

Thus, the compounds of the invention or the compounds obtained by the process of the invention, due to their unique biological properties, as shown in the above examples, are of high interest for use in the manufacture of a medicament.

Indeed, not only they have biological effects at least identical and even superior to Roscovitine but they have less or no interaction with pyridoxal kinase.

Otherwise stated, they may be used as active ingredient in a pharmaceutical composition. Their use is of high interest for the manufacture of medicament for the treatment of diseases in which an abnormal proliferation of cells, either tumoral or not, is involved. Such diseases are in particular a tumor, or leukemia or a non-tumoral but abnormal proliferation observed in various kidney diseases. But, due to their effects on CDK5 and their anti-apoptotic properties on differentiated cells, particularly neuronal cells, they may also be used in the treatment of a neurodegenerative disease such as Alzheimer's disease or Parkinson's disease, or in the treatment of stroke, ischemia and pain. Furthermore, they may also be used for the manufacture of a medicament for treating a viral disease due to their effect on CDK2 and CDK9.

Furthermore, they may be used in the manufacture of a medicament and in a method of treatment of renal diseases, in particular of such as mesangial proliferative glomerulonephritis, crescentic glomerulonephritis, collapsing glomerulopathy, proliferative lupus nephritis, polycystic kidney diseases, diabetic nephropathy and acute kidney injury as well as for treating inflammation, pleural inflammation, arthritis or glaucoma, due to their effects on CDK5, and apoptosis. They may also be used in the treatment of diabetes type II, given their effects on CDK5, and consequently their ability to increase insulin secretion in pancreatic cells.

The compounds of the invention or obtained by the process of the invention may be used for manufacturing a medicament or for treating a particular disease, either alone, or as a mixture of two or more compounds of the invention, or even in association with other compounds of the prior art known as having an effect on the particular disease to be treated.

The compounds of formula Ia-Iq are particularly appropriate in the treatment of the above cited diseases.

The present invention furthermore concerns a method of treatment or of prevention of a disease due to an abnormal proliferation of cells or of pain, which comprises at least one step consisting in administering to an individual in need thereof an effective amount of a compound of formula I or one of its salts, hydrates and stereoisomers.

The present invention at last provides a method of treatment or of prevention of a disease chosen among:
chronic lymphoid leukemia, chronic myeloid leukemia, tumor,
a neurodegenerative disease such as Parkinson's disease, Alzheimer's disease and stroke;
a viral disease,
a disease chosen among a kidney disease such as mesangial proliferative glomerulonephritis, crescentic glomerulonephritis, collapsing glomerulopathy, proliferative lupus nephritis, polycystic kidney diseases, diabetic nephropathy and acute kidney injury, cisplatin-induced nephrotoxicity;
an inflammation such as in pleural inflammation, arthritis, glaucoma, and
type 2 diabetes,
which comprises at least one step consisting in administering to an individual in need thereof an effective amount of a compound of formula I or one of its salts, hydrates and stereoisomers.

Within the invention, the term "prevent" intends to refer to a partial suppression of a risk of occurrence of an event, that is the risk of occurrence of a given, event is lower than before implementing the instant invention.

The invention claimed is:
1. Compounds having the following formula I:

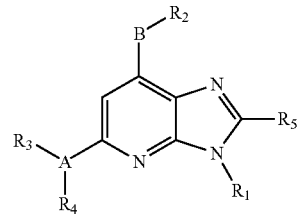

Formula I wherein:
A is CH or N,
$R_3$ is:
H, or
a $C_1$-$C_5$ alkyl group, or
=O, or
a ($C_1$-$C_3$) alkyl-C=O group in which the alkyl is optionally substituted by one or more halogen atoms, and/or hydroxy groups, and/or amino groups, and/or alkyloxy groups, and/or ketone groups,
$R_4$ is:
H, or
a $C_1$-$C_6$ alkyl group optionally substituted by one or more halogen atoms, and/or hydroxy groups, and/or amino groups, and/or alkyloxy groups, and/or ketone groups,

---

SEQUENCE LISTING

```
<160> NUMBER OF SEQ ID NOS: 2

<210> SEQ ID NO 1
<211> LENGTH: 26
<212> TYPE: PRT
<213> ORGANISM: Artificial Sequence
<220> FEATURE:
<221> NAME/KEY: MISC_FEATURE
<222> LOCATION: (21)..(21)
<223> OTHER INFORMATION: Synthetic construct - Phosphorylated Ser (21)

<400> SEQUENCE: 1

Tyr Arg Arg Ala Ala Val Pro Pro Ser Pro Ser Leu Ser Arg His Ser
1               5                   10                  15

Ser Pro His Gln Ser Glu Asp Glu Glu Glu
            20                  25

<210> SEQ ID NO 2
<211> LENGTH: 15
<212> TYPE: PRT
<213> ORGANISM: Artificial Sequence
<220> FEATURE:
<221> NAME/KEY: MISC_FEATURE
<222> LOCATION: (9)..(9)
<223> OTHER INFORMATION: Synthetic construct - Phosphorylated Ser (9)

<400> SEQUENCE: 2

Arg Arg Lys His Ala Ala Ile Gly Ser Ala Tyr Ser Ile Thr Ala
1               5                   10                  15
``` a C$_3$-C$_6$ cycloalkyl group optionally substituted by one or more halogen atoms, and/or hydroxy groups, and/or amino groups, and/or alkyloxy groups, and/or ketone groups, or a (C$_1$-C$_5$)alkyl(C$_3$-C$_6$)cycloalkyl group optionally substituted by one or more halogen atoms, and/or hydroxy groups, and/or amino groups, and/or alkyloxy groups, and/or ketone groups, or =O, or O=CCF$_3$, or a C$_1$-C$_6$ alkyl group substituted by an ester group, or an amino acyl group derived from natural, or non natural amino acids, or an acetyl group or a nicotynyl group, or A, R$_3$ and R$_4$ together form a C$_5$-C$_7$ cycloalkyl group, optionally containing one or more heteroatoms, B is O or S or NH, R$_1$ is:
  a C$_2$-C$_3$ alkyl optionally branched R$_2$ is:
  an aryl group optionally substituted by one or more halogen atoms, and/or hydroxy groups, and/or C$_1$-C$_3$ alkyloxy groups, and/or carboxylic acid groups, and/or carboxylic ester groups, and/or amine groups, and/or CF$_3$ groups, and/or optionally containing one or more heteroatoms, thus creating a 2-pyridyl group, or a 3-pyridyl group, or a 4-pyridyl group, or a 2-thienyl or a 3-thienyl group, or a methylbiaryl group, wherein each aryl cycle is optionally substituted by one or more halogen atoms, and/or hydroxy groups, and/or C$_1$-C$_3$ alkyloxy groups, and/or CF$_3$ groups, and/or carboxylic acid groups, and/or carboxylic ester groups, and/or amine groups, and/or optionally containing one or more heteroatoms, or a methylaryl group, the aryl cycle being optionally substituted by one or more halogen atoms, and/or hydroxy groups, and/or C$_1$-C$_3$ alkyloxy groups, and/or CF$_3$ groups, and/or optionally containing one or more heteroatoms, thus creating a 2-pyridyl group, or a 3-pyridyl group, or a 4-pyridyl group, or a 2-thienyl group or a 3-thienyl group, a biaryl group, each aryl cycle optionally containing one or more heteroatoms thus creating a 2-pyridyl group, or a 3-pyridyl group, or a 4-pyridyl group, or a 2-thienyl group or a 3-thienyl group, or each aryl cycle is optionally substituted by one or more halogen atoms, and/or hydroxy groups, and/or C$_1$-C$_3$ alkyloxy groups, and/or CF$_3$ groups, and/or carboxylic acid groups, and/or carboxylic ester groups, and/or amine groups, or B and R$_2$ together form a non aromatic cycle, R$_5$ is:
  a halogen atom, or
  a hydrogen atom, or
  a C$_1$-C$_5$ alkyl group optionally substituted by one or more hydroxy groups and/or amine groups and/or halogen atoms and/or carboxylic acid groups, or
  a (C$_1$-C$_4$)alkyl(C$_3$-C$_6$)cycloalkyl group in which the cycloalkyl group is optionally substituted by one or more hydroxy groups and/or amine groups and/or halogen atoms and/or carboxylic acid groups, and the salts, hydrates, and stereoisomers thereof.

2. Compounds according to claim 1 wherein, in Formula I, A is N.

3. Compounds according to claim 1 wherein, in Formula I, A is CH.

4. Compounds according to claim 1 wherein, in Formula I, B—R$_2$ is selected from the group consisting of:

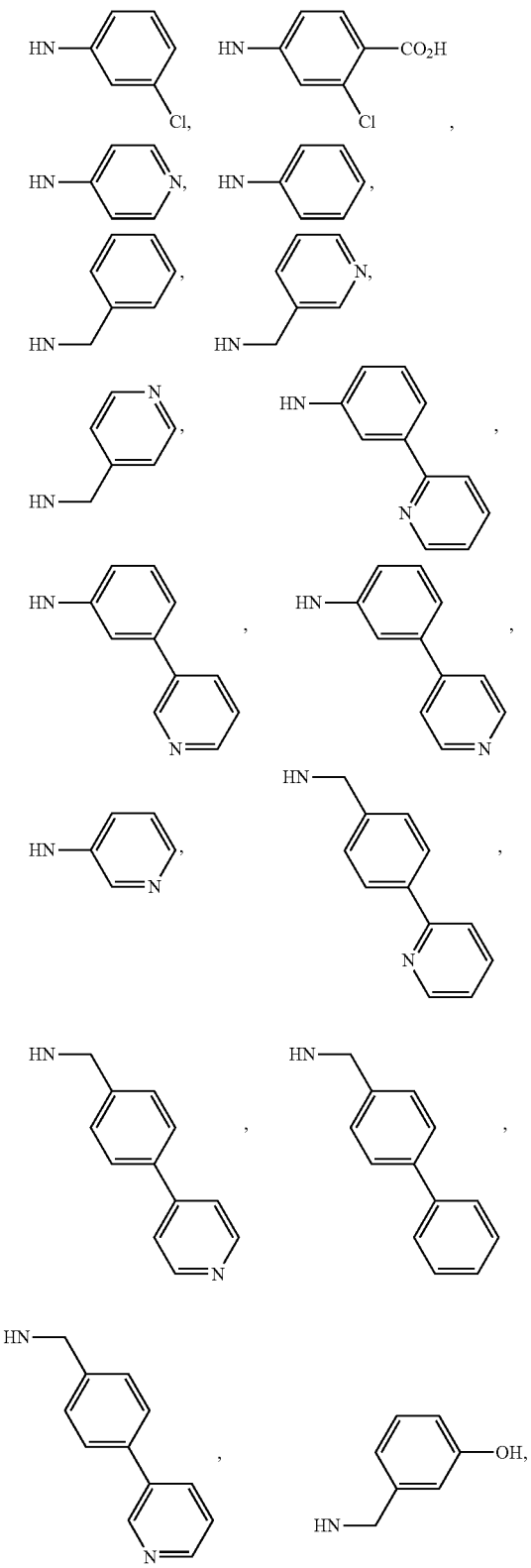

-continued
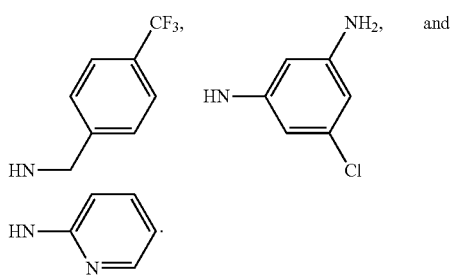
5. Compounds according to claim 1 wherein, in Formula I, $R_4$-A-$R_3$ is selected from the group consisting of:
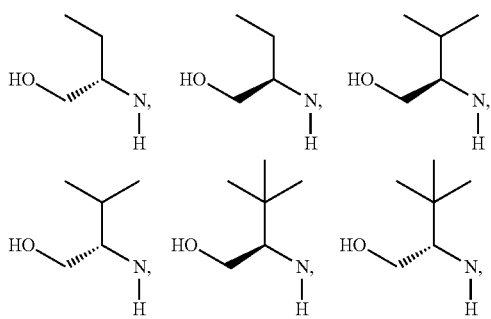
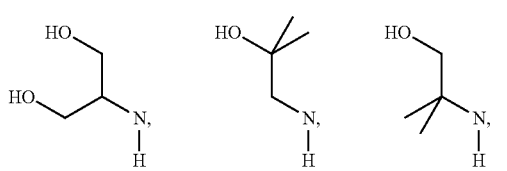
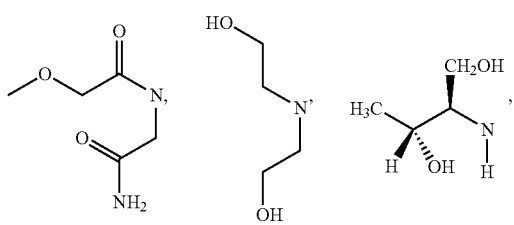
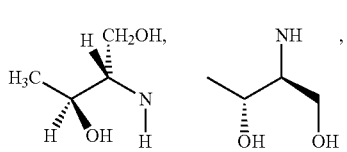
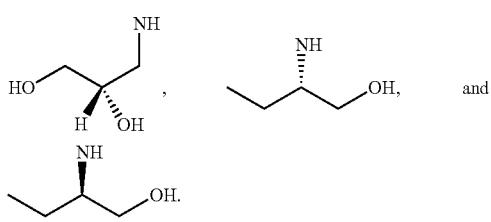
6. Compounds according to claim 1 wherein, in Formula I, $R_5$ is H.
7. Compounds having the following formulae:
Formula Ia
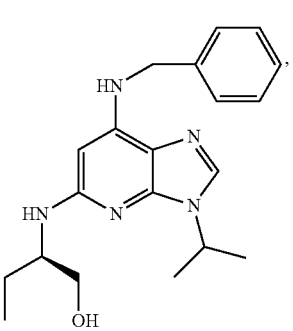
Formula Ib
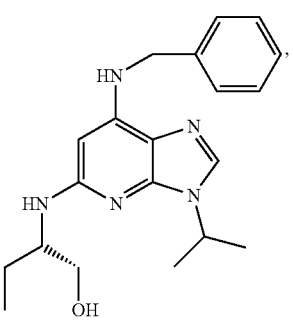
Formula Ic
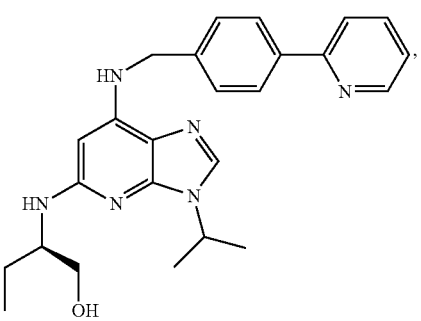
Formula Id
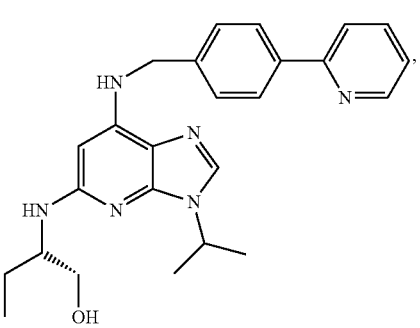
Formula Ie
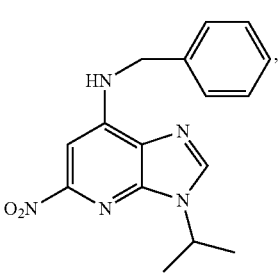

Formula If
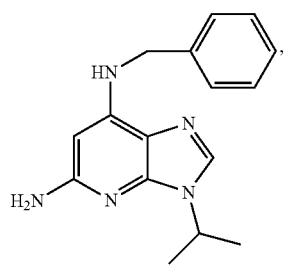
Formula Ig
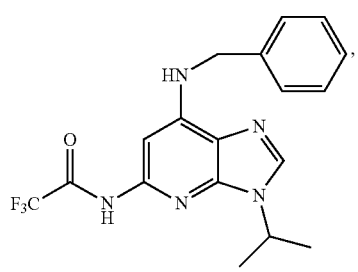
Formula Ih
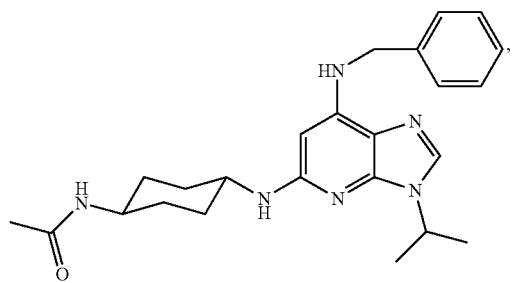
Formula Ii
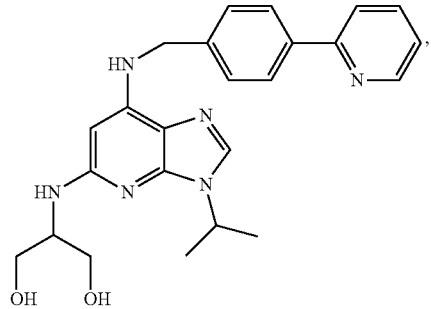
Formula Ij
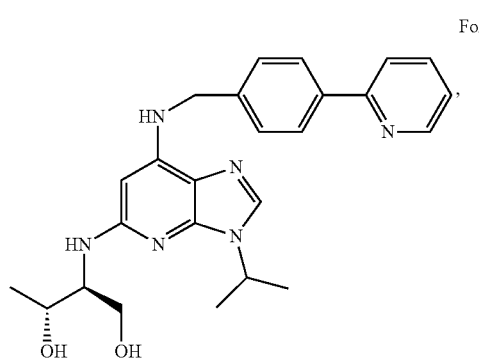
Formula Ik
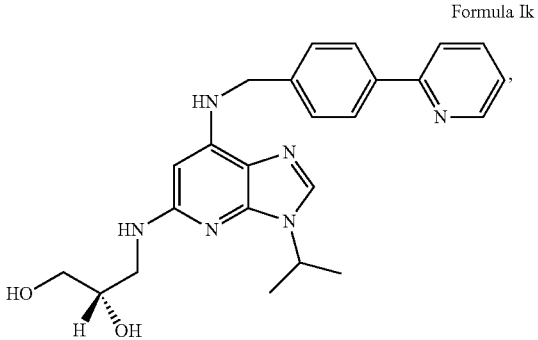
Formula Il
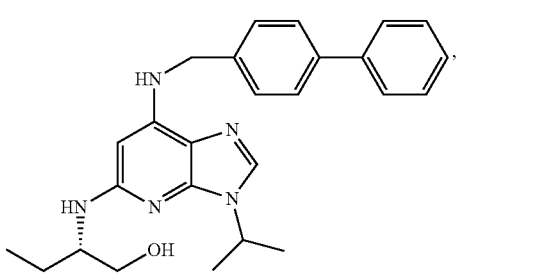
Formula Im
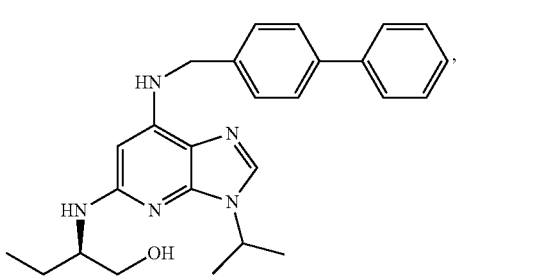
Formula In
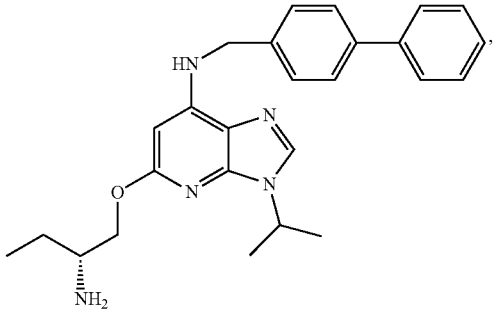
Formula Io
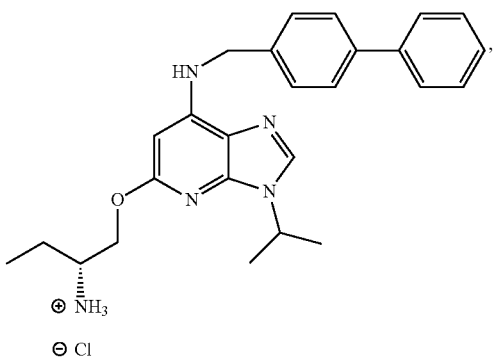

-continued

Formula Ip

Formula Iq

8. A process for manufacturing the compounds according to claim 2 comprising reacting a compound of the formula II:

Formula II wherein
B is O or S or NH,
$R_1$ is:
a $C_2$-$C_3$ alkyl, optionally branched
$R_2$ is:
an aryl group optionally substituted by one or more halogen atoms, and/or hydroxy groups, and/or $C_1$-$C_3$ alkyloxy groups, and/or carboxylic acid groups, and/or carboxylic ester groups, and/or amine groups, and/or $CF_3$ groups, and/or optionally containing one or more heteroatoms, thus creating a 2-pyridyl group, or a 3-pyridyl group, or a 4-pyridyl group, or a 2-thienyl or a 3-thienyl group, or
a methylbiaryl group, wherein each aryl cycle is optionally substituted by one or more halogen atoms, and/or hydroxy groups, and/or $C_1$-$C_3$ alkyloxy groups, and/or $CF_3$ groups, and/or carboxylic acid groups, and/or carboxylic ester groups, and/or amine groups, and/or optionally containing one or more heteroatoms, or
a methylaryl group, the aryl cycle being optionally substituted by one or more halogen atoms, and/or hydroxy groups, and/or $C_1$-$C_3$ alkyloxy groups, and/or $CF_3$ groups, and/or optionally containing one or more heteroatoms, thus creating a 2-pyridyl group, or a 3-pyridyl group, or a 4-pyridyl group, or a 2-thienyl group or a 3-thienyl group,
a biaryl group, each aryl cycle optionally containing one or more heteroatoms thus creating a 2-pyridyl group, or a 3-pyridyl group, or a 4-pyridyl group, or a 2-thienyl group or a 3-thienyl group, or each aryl cycle is optionally substituted by one or more halogen atoms, and/or hydroxy groups, and/or $C_1$-$C_3$ alkyloxy groups, and/or $CF_3$ groups, and/or carboxylic acid groups, and/or carboxylic ester groups, and/or amine groups,
or B and $R_2$ together form a non aromatic cycle,
$R_5$ is:
a halogen atom, or
a hydrogen atom, or
a $C_1$-$C_5$ alkyl group optionally substituted by one or more hydroxy groups and/or amine groups and/or halogen atoms and/or carboxylic acid groups, or
a $(C_1$-$C_4)$alkyl$(C_3$-$C_6)$cycloalkyl group in which the cycloalkyl group is optionally substituted by one or more hydroxy groups and/or amine groups and/or halogen atoms and/or carboxylic acid groups,
and X is Br, Cl, I or $NH_2$,
in a first alternative, with a compound of the following Formula III:

Formula III wherein,
A is N
$R_3$ is:
H, or
a $C_1$-$C_5$ alkyl group, or
=O, or
a $(C_1$-$C_3)$ alkyl-C=O group in which the alkyl is optionally substituted by one or more halogen atoms, and/or hydroxy groups, and/or amino groups, and/or alkyloxy groups, and/or ketone groups,
$R_4$ is:
H, or
a $C_1$-$C_6$ alkyl group optionally substituted by one or more halogen atoms, and/or hydroxy groups, and/or amino groups, and/or alkyloxy groups, and/or ketone groups,
a $C_3$-$C_6$ cycloalkyl group optionally substituted by one or more halogen atoms, and/or hydroxy groups, and/or amino groups, and/or alkyloxy groups, and/or ketone groups, or
a $(C_1$-$C_5)$alkyl$(C_3$-$C_6)$cycloalkyl group optionally substituted by one or more halogen atoms, and/or hydroxy groups, and/or amino groups, and/or alkyloxy groups, and/or ketone groups, or
=O, or
O=CCF$_3$ or
a $C_1$-$C_6$ alkyl group substituted by an ester group or an amino acyl group derived from natural, or non natural amino acids, or an acetyl group or a nicotynyl group,
or A, $R_3$ and $R_4$ together form a $C_5$-$C_7$ cycloalkyl group, optionally containing one or more heteroatoms, in presence of a catalyst selected from Pd(OAc)$_2$, Pd$_2$dba$_3$ or CuI, optionally in presence of a ligand selected from a ligand Binap or ethyleneglycol under basic conditions, or in a second alternative with a compound of the following Formula IV:

Y—R$_6$     Formula IV in which Y is I, Br or C$_1$ and R$_6$ is R$_3$ or R$_4$, for obtaining a compound of the following formula V:

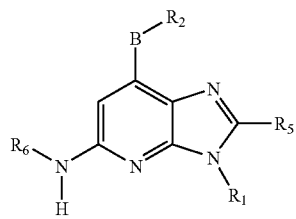

Formula V optionally followed, when R$_3$ and R$_4$ are different from H, by a step of coupling the compound of Formula V with a compound of the following Formula VI:

Y—R$_7$     Formula VI in which Y is I, Br or C$_1$ and R$_7$ is R$_3$ when R$_6$ is R$_4$ or R$_7$ is R$_4$ when R$_6$ is R$_3$, said coupling steps being carried out in presence of a catalyst selected from Pd(OAc)$_2$, Pd$_2$dba$_3$ or CuI, optionally in the presence of a ligand Binap, under basic conditions.

9. A pharmaceutical composition comprising at least one compound having the following formula I:

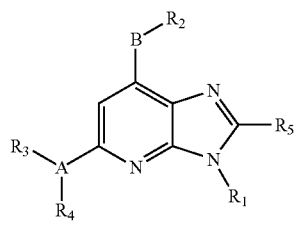

Formula I wherein:
A is CH or N,
R$_3$ is:
  H, or
  a C$_1$-C$_5$ alkyl group, or
  =O, or
  a (C$_1$-C$_3$) alkyl-C=O group in which the alkyl is optionally substituted by one or more halogen atoms, and/or hydroxy groups, and/or amino groups, and/or alkyloxy groups, and/or ketone groups,
R$_4$ is:
  H, or
  a C$_1$-C$_6$ alkyl group optionally substituted by one or more halogen atoms, and/or hydroxy groups, and/or amino groups, and/or alkyloxy groups, and/or ketone groups, or
  a C$_3$-C$_6$ cycloalkyl group optionally substituted by one or more halogen atoms, and/or hydroxy groups, and/or amino groups, and/or alkyloxy groups, and/or ketone groups, or a (C$_1$-C$_5$)alkyl(C$_3$-C$_6$)cycloalkyl group optionally substituted by one or more halogen atoms, and/or hydroxy groups, and/or amino groups, and/or alkyloxy groups, and/or ketone groups, or =O, or O=CCF$_3$, or a C$_1$-C$_6$ alkyl group substituted by an ester group, or an amino acyl group derived from natural, or non natural amino acids, or an acetyl group or a nicotynyl group, or A, R$_3$ and R$_4$ together form a C$_5$-C$_7$ cycloalkyl group, optionally containing one or more heteroatoms, B is O or S or NH, R$_1$ is:
  a C$_2$-C$_3$ alkyl optionally branched R$_2$ is:
  an aryl group optionally substituted by one or more halogen atoms, and/or hydroxy groups, and/or C$_1$-C$_3$ alkyloxy groups, and/or carboxylic acid groups, and/or carboxylic ester groups, and/or amine groups, and/or CF$_3$ groups, and/or optionally containing one or more heteroatoms, thus creating a 2-pyridyl group, or a 3-pyridyl group, or a 4-pyridyl group, or a 2-thienyl or a 3-thienyl group, or a methylbiaryl group, wherein each aryl cycle is optionally substituted by one or more halogen atoms, and/or hydroxy groups, and/or C$_1$-C$_3$ alkyloxy groups, and/or CF$_3$ groups, and/or carboxylic acid groups, and/or carboxylic ester groups, and/or amine groups, and/or optionally containing one or more heteroatoms, or a methylaryl group, the aryl cycle being optionally substituted by one or more halogen atoms, and/or hydroxy groups, and/or C$_1$-C$_3$ alkyloxy groups, and/or CF$_3$ groups, and/or optionally containing one or more heteroatoms, thus creating a 2-pyridyl group, or a 3-pyridyl group, or a 4-pyridyl group, or a 2-thienyl group or a 3-thienyl group, a biaryl group, each aryl cycle optionally containing one or more heteroatoms thus creating a 2-pyridyl group, or a 3-pyridyl group, or a 4-pyridyl group, or a 2-thienyl group or a 3-thienyl group, or each aryl cycle is optionally substituted by one or more halogen atoms, and/or hydroxy groups, and/or C$_1$-C$_3$ alkyloxy groups, and/or CF$_3$ groups, and/or carboxylic acid groups, and/or carboxylic ester groups, and/or amine groups, or B and R$_2$ together form a non aromatic cycle, R$_5$ is:
  a halogen atom, or
  a hydrogen atom, or
  a C$_1$-C$_5$ alkyl group optionally substituted by one or more hydroxy groups and/or amine groups and/or halogen atoms and/or carboxylic acid groups, or
  a (C$_1$-C$_4$)alkyl(C$_3$-C$_6$)cycloalkyl group in which the cycloalkyl group is optionally substituted by one or more hydroxy groups and/or amine groups and/or halogen atoms and/or carboxylic acid groups, and the salts, hydrates, and stereoisomers thereof.

10. A method of treatment of a disease comprising at least one step of administering to an individual in need thereof an effective amount of a compound of formula I according to claim 1 or its salts, hydrates and stereoisomers, wherein the disease is selected from the group consisting of:

- chronic lymphoid leukemia, and chronic myeloid leukemia,
- a neurodegenerative disease selected from the group consisting of Parkinson's disease, Alzheimer's disease and stroke;
- a viral disease selected from the group consisting of HIV, Herpes, and HCMV,
- a kidney disease selected from the group consisting of mesangial proliferative glomerulonephritis, crescentic glomerulonephritis, collapsing glomerulopathy, proliferative lupus nephritis, polycystic kidney diseases, diabetic nephropathy and acute kidney injury, and cisplatin-induced nephrotoxicity;
- an inflammation selected from the group consisting of pleural inflammation, arthritis, and glaucoma, and
- type 2 diabetes.

11. A method of treatment of pain which comprises at least one step of administering to an individual in need thereof an effective amount of a compound of formula I according to claim 1 or one of its salts, hydrates and stereoisomers.

12. A method of treatment of pain or a disease selected from the group consisting of:

- chronic lymphoid leukemia, chronic myeloid leukemia,
- a neurodegenerative disease selected from the group consisting of Parkinson's disease, Alzheimer's disease and stroke;
- a viral disease selected from the group consisting of HIV, Herpes, and HCMV,
- a kidney disease selected from the group consisting of mesangial proliferative glomerulonephritis, crescentic glomerulonephritis, collapsing glomerulopathy, proliferative lupus nephritis, polycystic kidney diseases, diabetic nephropathy and acute kidney injury, and cisplatin-induced nephrotoxicity;
- inflammation selected from the group consisting of pleural inflammation, arthritis, and glaucoma, and
- type 2 diabetes comprising administering to an individual in need thereof an effective amount of a compound selected from the group consisting of

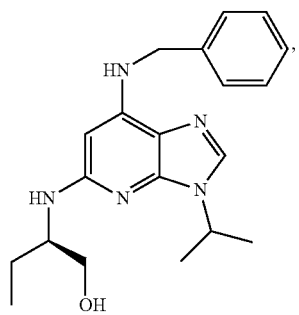

Formula Ia

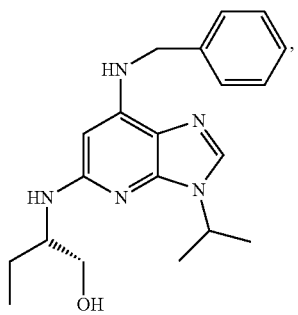

Formula Ib

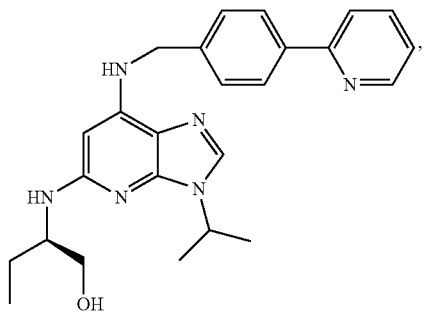

Formula Ic

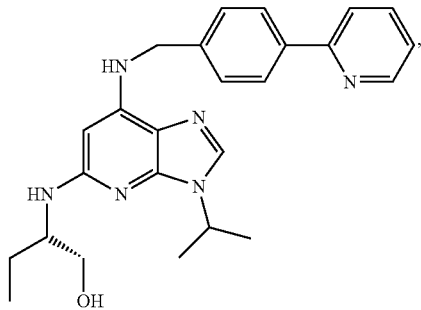

Formula Id

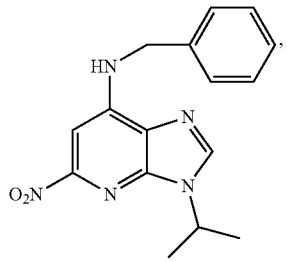

Formula Ie

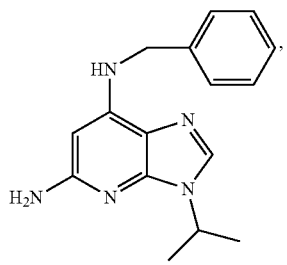

Formula If

Formula Ig
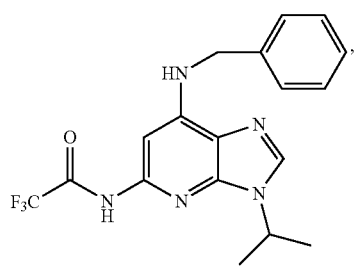
Formula Ih
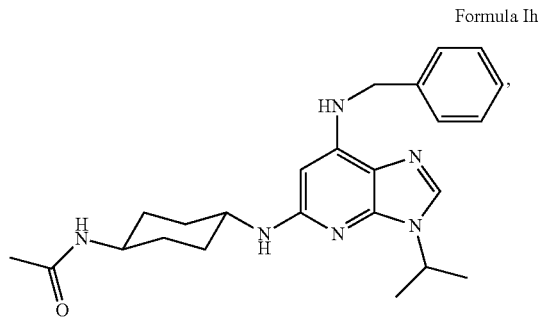
Formula Ii
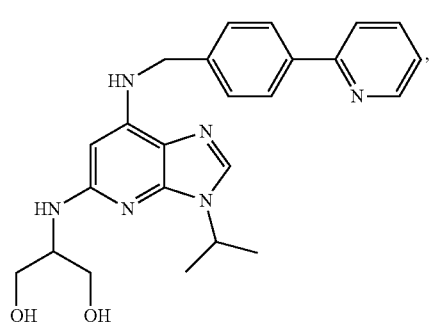
Formula Ij
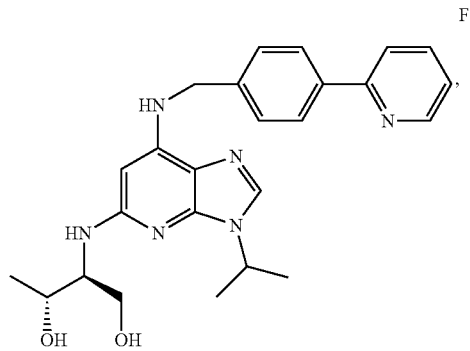
Formula Ik
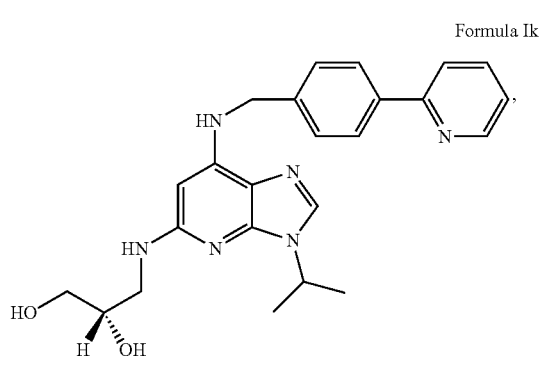
Formula Il
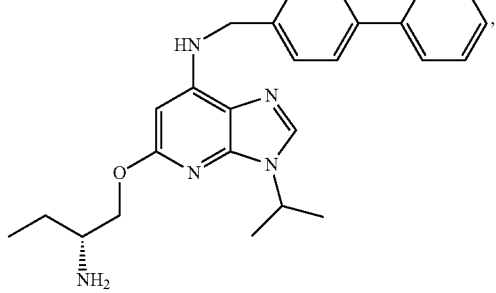
Formula Im
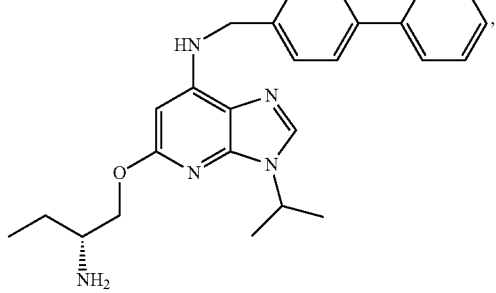
Formula In
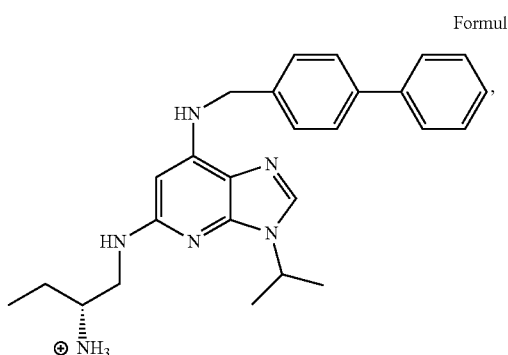
Formula Io
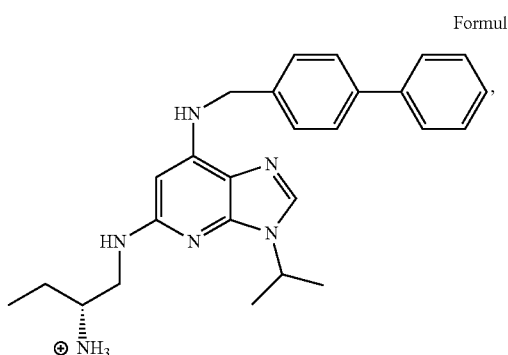
Formula Ip and
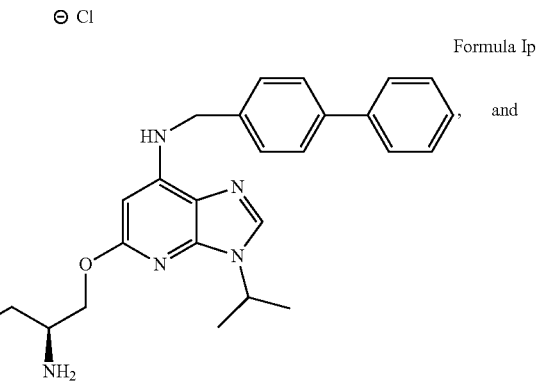

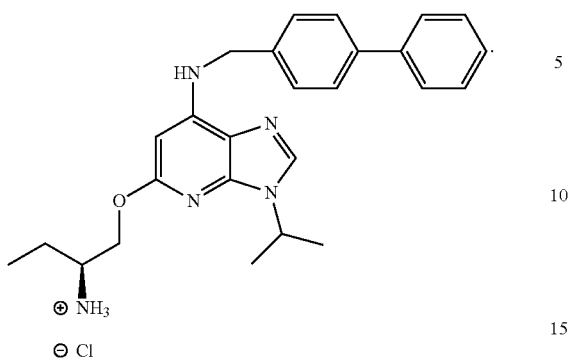

Formula Iq

13. Compounds according to claim 1 wherein, in Formula I, $R_1$ is isopropyl.

14. Compositions according to claim 9 wherein, in Formula I, $R_1$ is isopropyl.

15. A method of inhibiting the growth of cell lines selected from the group consisting of SH-SY5Y, HEK293, LS 174T, and HCT116, comprising administering to the cell lines an effective amount of the compound of formula I according to claim 1 or the salts, hydrates or stereoisomers thereof.

* * * * *